United States Patent
Grodzins et al.

(10) Patent No.: US 7,010,094 B2
(45) Date of Patent: Mar. 7, 2006

(54) X-RAY INSPECTION USING SPATIALLY AND SPECTRALLY TAILORED BEAMS

(75) Inventors: Lee Grodzins, Lexington, MA (US); Peter Rothschild, Boston, MA (US); Roderick D. Swift, Belmont, MA (US)

(73) Assignee: American Science and Engineering, Inc., Billerica, MA (US)

( * ) Notice: Subject to any disclaimer, the term of this patent is extended or adjusted under 35 U.S.C. 154(b) by 249 days.

(21) Appl. No.: 10/161,037

(22) Filed: May 31, 2002

(65) Prior Publication Data

US 2003/0016790 A1    Jan. 23, 2003

Related U.S. Application Data

(63) Continuation-in-part of application No. 09/919,352, filed on Jul. 30, 2001, now abandoned, which is a continuation-in-part of application No. 09/502,093, filed on Feb. 10, 2000, now Pat. No. 6,459,761.

(51) Int. Cl.
  *G21K 1/02*    (2006.01)
(52) U.S. Cl. .................. 378/157; 378/160; 378/145
(58) Field of Classification Search ............... 378/57, 378/58, 147, 156, 157, 160, 145, 146, 148, 378/150, 158, 19, 98.8; 250/358.1
  See application file for complete search history.

(56) References Cited

U.S. PATENT DOCUMENTS

| | | | |
|---|---|---|---|
| 3,748,487 A | | 7/1973 | Edholm et al. |
| 3,917,954 A | * | 11/1975 | Boge ........................... 378/159 |
| 3,919,467 A | | 11/1975 | Peugeot |
| 4,255,664 A | * | 3/1981 | Rutt et al. ...................... 378/5 |
| 4,780,897 A | * | 10/1988 | McDaniel et al. ............ 378/62 |
| 5,007,072 A | * | 4/1991 | Jenkins et al. ................. 378/88 |
| 5,040,199 A | | 8/1991 | Stein |
| 5,278,887 A | * | 1/1994 | Chiu et al. .................. 378/156 |
| 5,394,454 A | | 2/1995 | Harding |
| 5,412,704 A | | 5/1995 | Horbaschek |
| 5,600,700 A | | 2/1997 | Krug et al. |

(Continued)

FOREIGN PATENT DOCUMENTS

EP          382560          8/1990

(Continued)

OTHER PUBLICATIONS

U.S. Appl. No. 09/395,331, filed Sep. 13, 1999.

(Continued)

*Primary Examiner*—Edward J. Glick
*Assistant Examiner*—Irakli Kiknadze
(74) *Attorney, Agent, or Firm*—Bromberg & Sunstein LLP

(57) ABSTRACT

A system and method for inspecting an object, the system and method comprising a source for generating a penetrating radiation beam for irradiating the object, the beam having, for each instant of time, an instantaneous energy spectrum of intensity, a shaper for modulating the generated beam, thereby creating a shaped beam, the shaper comprising at least a first section and a second section, the first section attenuating the intensity of a portion of the generated beam by a first attenuation factor and the second section attenuating the intensity of another portion of the generated beam by a second attenuation factor, and at least one detector for detecting the shaped beam after the shaped beam interacts with the object. The source may scan a beam across an object while the source and at least one detector are moving on a platform capable of highway travel or on an inspection module movable with respect to the object.

7 Claims, 16 Drawing Sheets

U.S. PATENT DOCUMENTS

| | | | |
|---|---|---|---|
| 5,677,943 A * | 10/1997 | Hoebel | 378/156 |
| 5,692,028 A * | 11/1997 | Geus et al. | 378/57 |
| 5,768,334 A | 6/1998 | Maitrejean et al. | |
| 5,805,660 A | 9/1998 | Perion et al. | |
| 5,838,759 A | 11/1998 | Armistead | |
| 5,940,468 A | 8/1999 | Huang et al. | |
| 6,192,101 B1 | 2/2001 | Grodzins | |
| 6,278,115 B1 * | 8/2001 | Annis et al. | 250/363.01 |
| 6,285,740 B1 * | 9/2001 | Seely et al. | 378/98.9 |
| 6,307,918 B1 * | 10/2001 | Toth et al. | 378/158 |

FOREIGN PATENT DOCUMENTS

| | | |
|---|---|---|
| EP | 496438 | 7/1992 |
| EP | 981999 | 3/2000 |
| WO | WO97/18462 | 5/1997 |
| WO | WO99/09400 | 2/1999 |
| WO | WO99/33064 | 7/1999 |
| WO | WO99/39189 | 8/1999 |
| WO | WO00/33060 | 7/2000 |

OTHER PUBLICATIONS

PCT/US/01/04143, filed Sep. 2, 2001.

Patent Abstracts of Japan, vol. 018, No. 403, JP 06 119989 A (Shimadzu Corp.), Apr. 28, 1994, abstract, Jul. 27, 1994.

Patent Abstracts of Japan, vol. 1999, No. 03, JP 10 314154 A (Hitachi Medical Corp.), Dec. 2, 1998, abstract, Mar. 31, 1999.

* cited by examiner

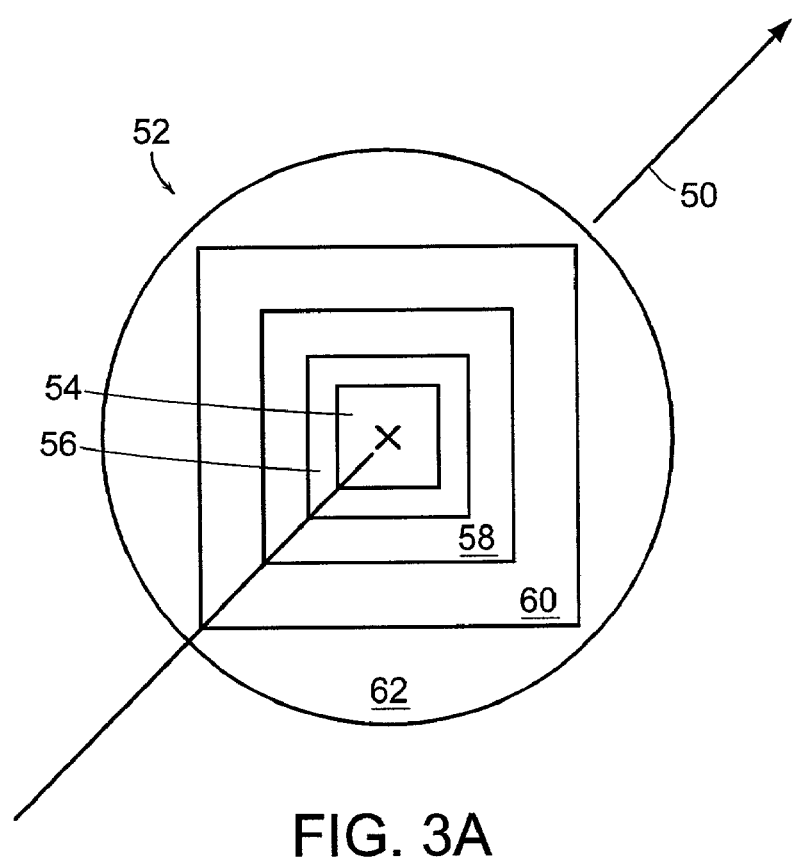
FIG. 3A
FIG. 3B

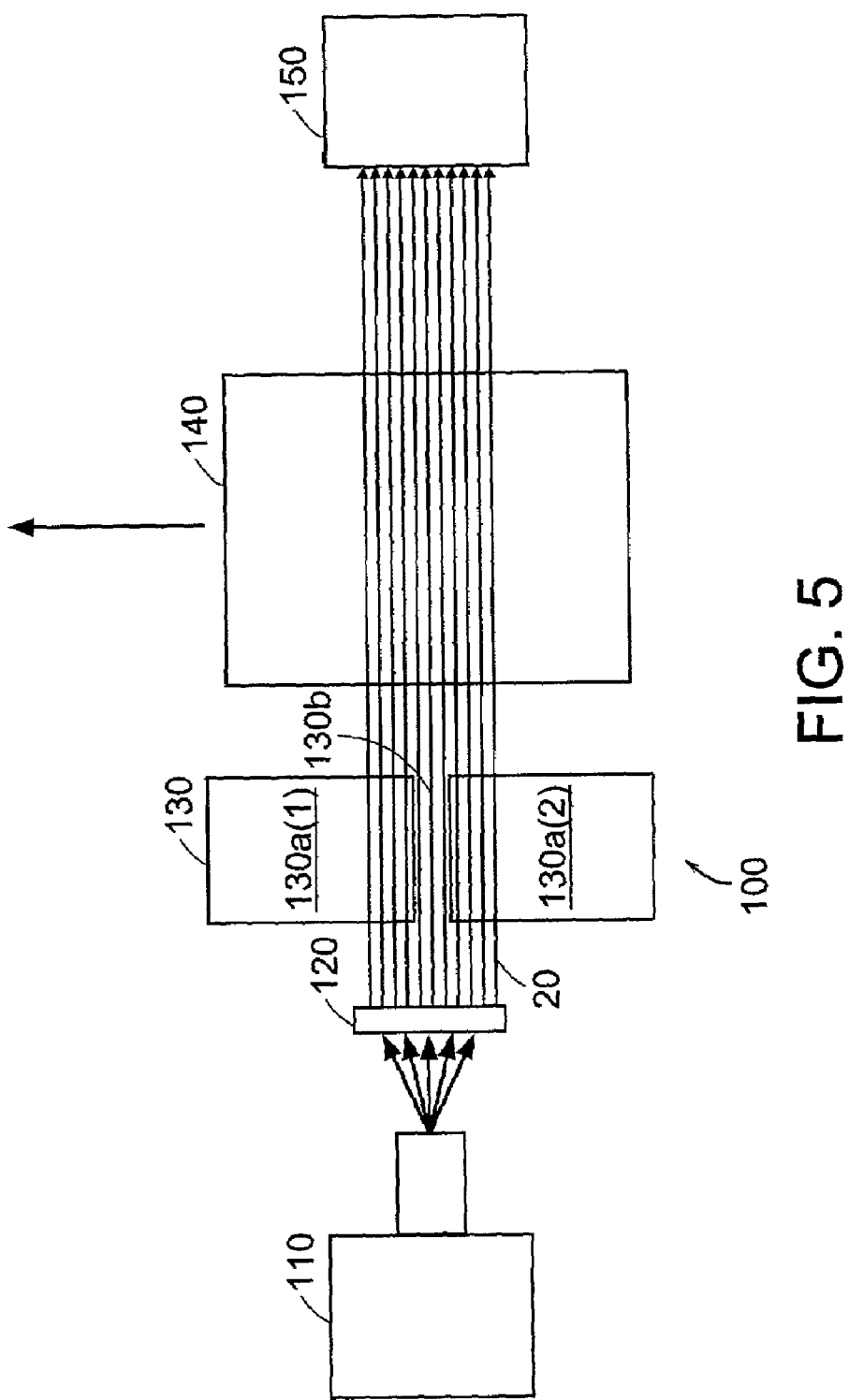

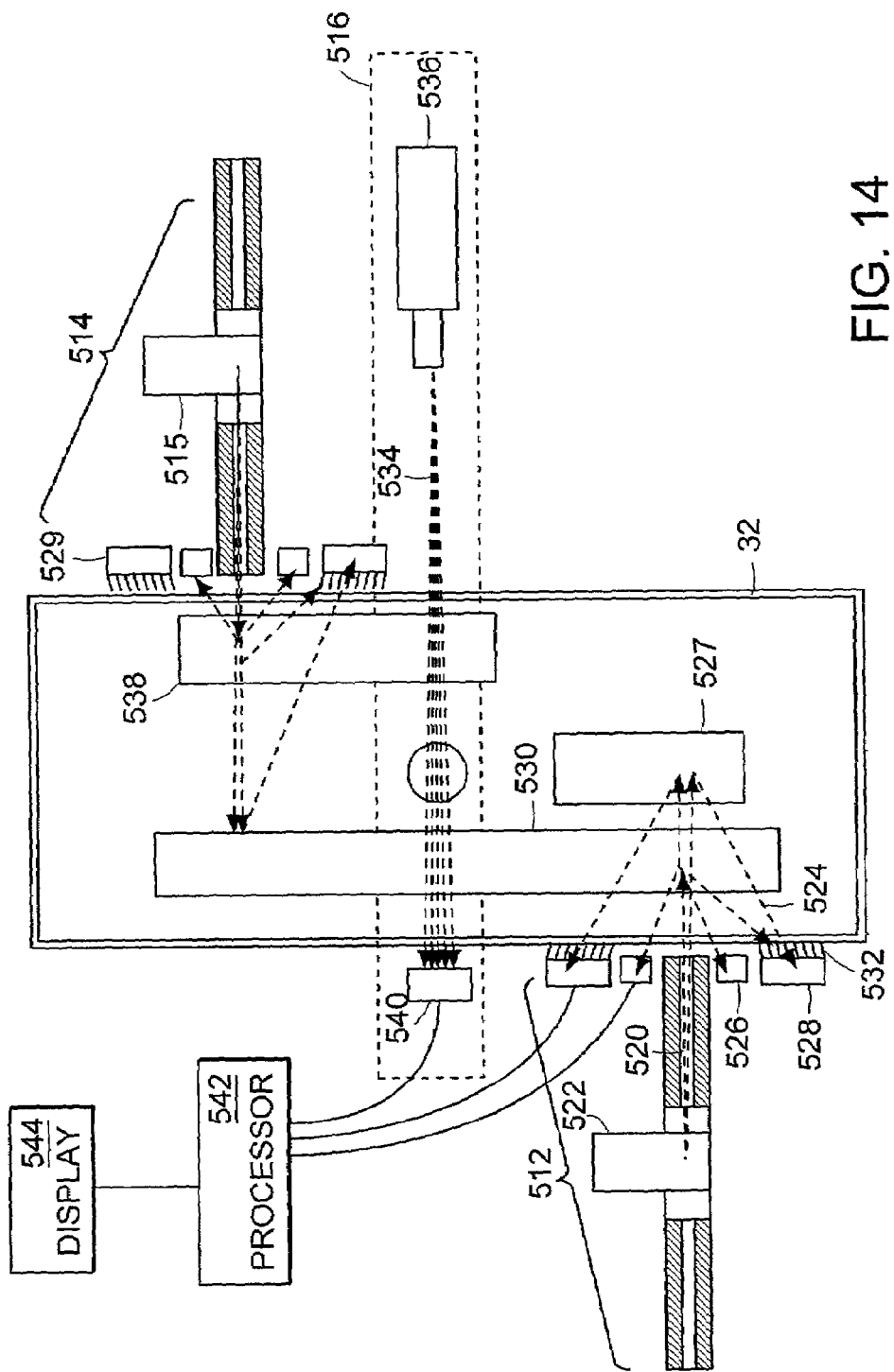

X-RAY INSPECTION USING SPATIALLY AND SPECTRALLY TAILORED BEAMS

CROSS REFERENCE TO RELATED APPLICATIONS

This application is a continuation-in-part of U.S. patent application Ser. No. 09/502,093, filed Feb. 10, 2000, now U.S. Pat. No. 6,459,761 entitled SPECTRALLY SHAPED X-RAY INSPECTION SYSTEM and of U.S. patent application Ser. No. 09/919,352, filed Jul. 30, 2001, now abandoned entitled A SYSTEM AND METHOD FOR INSPECTING AN OBJECT USING SPATIALLY AND SPECTRALLY DISTINGUISHED BEAMS, the disclosures of both of which are incorporated herein, in their entirety, by reference.

TECHNICAL FIELD

The present invention relates to systems and methods for inspecting objects and, more particularly, the invention relates to systems and methods for inspecting objects with radiation beams tailored to provide optimized cross-sectional profiles.

BACKGROUND OF THE INVENTION

X-ray inspection systems, such as those used to characterize the contents of concealing enclosures such as baggage or cargo containers, typically employ an irradiating beam of specified cross-section that is swept relative to an object while portions of the beam that are either transmitted through the object or scattered by it are detected. Cross-sectional shapes of beams typically employed include fan beams, otherwise referred to as 'fan-shaped' beams, and pencil beams, where the characteristic dimension of the beam governs the spatial resolution of the system. The irradiating beam is characterized by an energy distribution of x-rays that is governed by the nature of the x-ray source and is invariant across the entire cross-section of the beam.

For a specified set of beam characteristics, the total photon flux through an object scales with the area of the beam. Thus, higher resolution, achieved by virtue of a tighter beam, is achieved at the expense of photon flux. Therefore, the thickness of the object through which radiation can be detected with a useful signal-to-noise ratio is also limited unless other parameters are changed. In the prior art, this trade-off is part of the design of the system that is performed prior to its operation in the field.

SUMMARY OF THE INVENTION

In accordance with preferred embodiments of the present invention, there is provided a graduated collimator for providing a beam of increasing average energy as a function of distance measured from a central axis. The collimator has a plurality of concentric areas, each of the areas defined in a plane substantially perpendicular to the central axis, such that any specified area is characterized by an opacity to the beam exceeding that of any area interior to the specified area.

In accordance with other embodiments of the invention, at least one of the plurality of concentric areas may be the surface of an x-ray attenuating material, and the plurality of concentric areas may include a central area of substantially no attenuation. A subset of the concentric areas may be surfaces of frames of radially increasing opacity.

In accordance with another aspect of the invention, a system is provided for inspecting an object. The system has a source for generating a penetrating radiation beam for irradiating the object, and the beam has an instantaneous power spectrum of intensity as a function of energy at any given instant of time. The system also has a shaper for modulating the generated beam, thereby creating a shaped beam, the shaper comprising at least a first section and a second section, the first section attenuating the intensity of a portion of the generated beam by a first attenuation factor and the second section attenuating the intensity of another portion of the generated beam by a second attenuation factor. Finally, the system has at least one detector for detecting the shaped beam after the shaped beam interacts with the object. The first attenuation factor may be 1. The detector or detectors may detect photons of energies exceeding a first fiducial energy as well as photons of energies exceeding a second fiducial energy, and may operate in an energy-dispersive mode or a current mode.

The shaper may spatially separate the shaped beam into a first beam and a second beam, the first beam including the portion of the generated beam attenuated in the first section of the shaper and the second beam including the portion of the generated beam attenuated in the second section of the shaper. One or more detectors may then detect the first beam after the first beam interacts with the object, while another detector detects the second beam after the second beam interacts with the object. One or more detectors may also detect photons of energies in the first beam exceeding a first fiducial energy while another detector detects photons of energies in the second beam exceeding a second fiducial energy.

The shaper may be configured in such a manner as to reduce ambient radiation dose. A first section of the shaper may include an element having an atomic number greater than 23.

In accordance with other embodiments of the invention, an inspection system is provided for inspecting an object, wherein the system has a source, a shaper, and two detectors. The source generates a penetrating radiation beam for irradiating the object, the beam having, at each instant of time, an instantaneous energy spectrum. The shaper modulates the generated beam, thereby creating a shaped beam, and has at least a first section and a second section, the first section attenuating the intensity of a portion of the generated beam by a first attenuation factor and the second section attenuating the intensity of another portion of the generated beam by a second attenuation factor. The first detector detects the shaped beam attenuated by the first attenuation factor after the shaped beam interacts with the object while the second detector detects the shaped beam attenuated by the second attenuation factor after the shaped beam interacts with the object. The first attenuation factor may be 1, and the first detector may detect photons of energies exceeding a first fiducial energy while the second detector detects photons of energies exceeding a second fiducial energy. The first and second detectors may be arranged in tandem.

In accordance with yet further embodiments of the invention, an inspection system for inspecting an object may be provided having a bed moveable along a first direction having a horizontal component, and a source coupled to move with the bed for generating a penetrating radiation beam for irradiating the object, the beam having, at each instant of time, an instantaneous power spectrum of intensity as a function of energy. The system has a motorized drive for moving the bed in the first direction such that the beam is caused to traverse the object as the bed is moved. The system also has a shaper for modulating the generated beam, thereby creating a shaped beam, the shaper comprising at least a first section and a second section, the first section attenuating the intensity of a portion of the generated beam by a first attenuation factor and the second section attenuating the intensity of another portion of the generated beam by a second attenuation factor. Finally, the inspection system has a detector for detecting the shaped beam after the shaped beam interacts with the object, the detector coupled such that the detector moves in coordination with the bed.

a. An inspection system may be provided wherein the source of penetrating radiation is coupled to a self-propelled vehicle capable of on-road travel, where the vehicle has one drive train for propelling the vehicle for on-road travel and another drive train, distinct from the first drive train, for propelling the vehicle in a first direction during inspection of the object. This system has a shaper for modulating the generated beam, thereby creating a shaped beam, the shaper comprising at least a first section and a second section, the first section attenuating the intensity of a portion of the generated beam by a first attenuation factor and the second section attenuating the intensity of another portion of the generated beam by a second attenuation factor. The system has a detector for detecting the shaped beam after the shaped beam interacts with the object, the detector coupled such that the detector moves in coordination with the bed.

Finally, an inspection system may be provided for inspecting an object, in accordance with the invention, that has a movable bed capable of traversing the object and a source coupled to the movable bed for generating a penetrating radiation beam for irradiating the object, where the beam has, at each instant of time, an instantaneous power spectrum of intensity as a function of energy. The inspection system has a shaper for modulating the generated beam, thereby creating a shaped beam, the shaper comprising at least a first section and a second section, the first section attenuating the intensity of a portion of the generated beam by a first attenuation factor and the second section attenuating the intensity of another portion of the generated beam by a second attenuation factor. Finally, the inspection system has a detector for detecting the shaped beam after the shaped beam interacts with the object, the detector coupled such that the detector moves in coordination with the bed. At least one scatter detector may be coupled so as to move in coordination with the bed.

BRIEF DESCRIPTION OF THE DRAWINGS

The foregoing features of the invention will be more readily understood by reference to the following detailed description, taken with reference to the accompanying drawings, in which:

FIG. 3A shows a frontal view of a graduated collimating aperture for shaping a beam in accordance with preferred embodiments of the present invention;

FIG. 3B shows a cross-sectional side view of a graduated collimating aperture for shaping a beam in accordance with embodiments of the present invention;

FIG. 5 is a schematic top view of an exemplary embodiment of an inspection system in accordance with the invention using a shaper to attenuate portions of a radiation beam using different attenuation factors and a detector to detect the shaped beam;

FIG. 12A shows the cargo container inspection system of FIG. 9A, as deployed for inspection of a full-sized tractor-trailer, while

FIG. 14 is a schematic top view of an x-ray inspection configuration employing independent transmission and backscatter systems in accordance with embodiments of the present invention.

DETAILED DESCRIPTION OF SPECIFIC EMBODIMENTS

Figure 1:
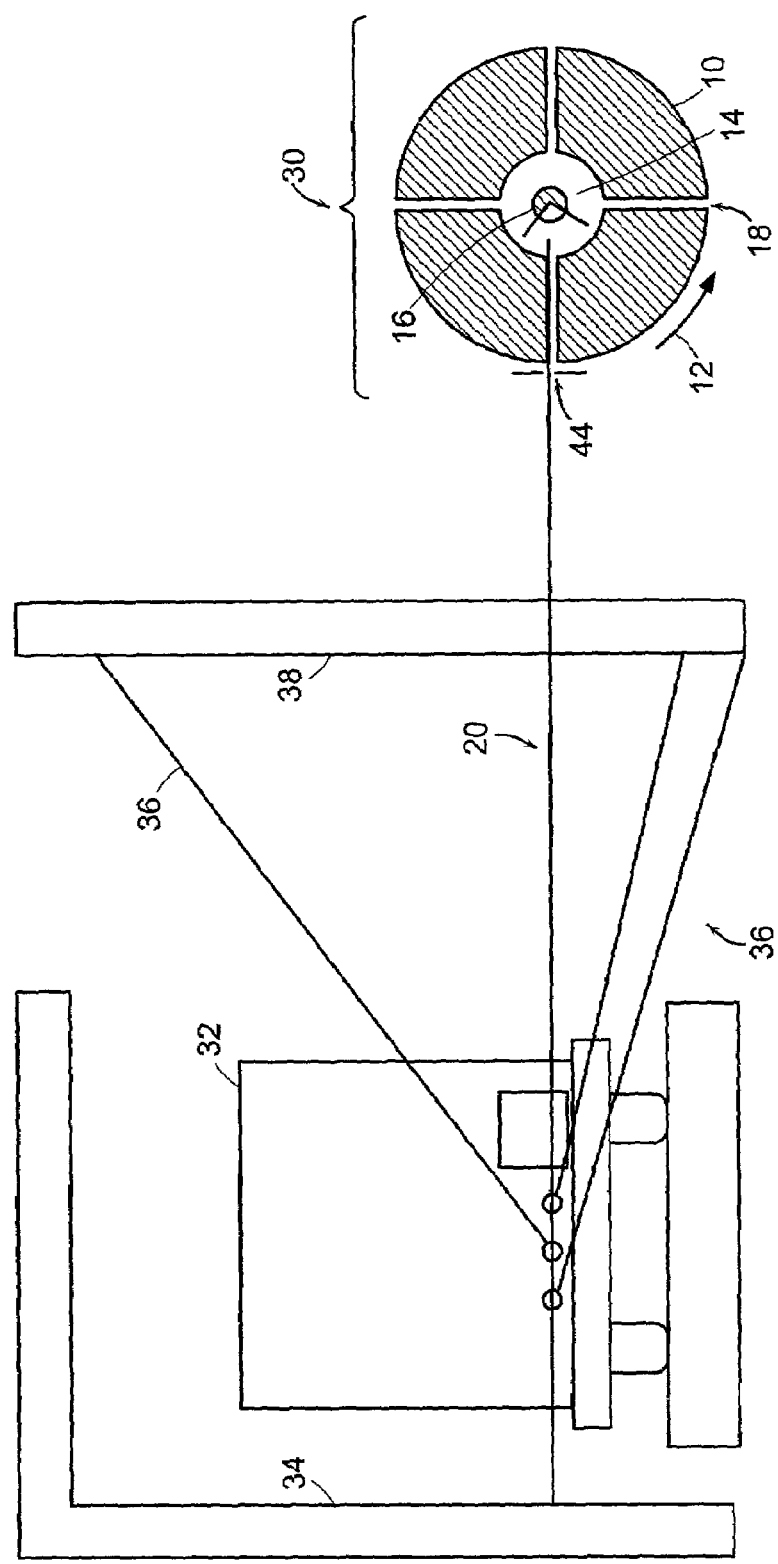
FIG. 1 is a schematic cross-sectional view of an exemplary embodiment of an inspection system using a collimated pencil beam in accordance with the invention.

As discussed in U.S. patent application Ser. No. 09/502,093, the design of an x-ray inspection system to examine heterogeneous cargo requires joint consideration of conflicting requirements for penetration, radiation dosage, and sensitivity. For example, the high-energy x-ray components of a radiation beam from a 3 MeV x-ray accelerator penetrate approximately 3 times farther through iron than do the high-energy x-ray components of a radiation beam from a 450 keV x-ray accelerator. However, radiation dosage, that is, the integrated radiated energy, increases as the electron energy from an x-ray accelerator is raised. For example, the radiation dose from a 3 MeV x-ray accelerator operating at 100 microamps is about 5 times greater than the radiation dose from a 450 keV x-ray accelerator operating at 10 mA. In addition, the high-energy x-ray components of a radiation beam are not as "sensitive" for distinguishing among materials as the low-energy x-ray components of a radiation beam, in the sense in which sensitivity is the detected change in transmitted countrate per unit thickness of a specified material.

One measure of the ability of an x-ray inspection system to detect "contraband" is the minimum thickness of material that can be detected. In determining that minimum thickness, consider a mono-energetic beam of photons penetrating an object having thickness T. The object has a linear absorption co-efficient $\lambda(E,Z)$, which is a function of the material and the energy of the photons that penetrate the object. If $N_O(E)$ is the number of x-ray photons incident on the object, then N(E), the number of x-ray photons emerging from the object, is given by:

$$N(E) = N_O(E) e^{-\lambda T} \quad \text{(Eqn. 1)}$$

To determine the minimum thickness, $\Delta T$, that can be detected, differentiate Eqn. 1:

$$\frac{\Delta N}{\Delta T} = -N_O \lambda e^{-\lambda T} \quad \text{(Eqn. 2)}$$

The relative change in count rate per thickness is:

$$\frac{\Delta N}{N \Delta T} = -\lambda \quad \text{(Eqn. 3)}$$

The minimal detectable signal may be taken to be 3 times the standard deviation of the signal (or 6 times the standard deviation, with Eqns. 4 and 5 changed mutatis mutandis):

$$\Delta N = 3\sqrt{N} \quad \text{(Eqn. 4)}$$

Substituting Eqn. 4 into Eqn. 3 yields the minimum thickness that can be detected for a given number of detected counts:

$$|\Delta T| = \frac{3}{\lambda \sqrt{N}} \quad \text{(Eqn. 5)}$$

Thus, the minimum detectable thickness, for a given pixel, varies inversely with the square root of the counts in the detector and inversely with the linear attenuation coefficient $\lambda$.

The linear attenuation coefficient for iron is 8.8 cm$^{-1}$ at 60 keV, the energy of the strong, characteristic x-ray beams from a tungsten anode. As the energy of the photon increases, $\lambda(F_e)$ drops rapidly, for example, at 200 keV, $\lambda(F_e)$ is 1.1 cm$^{-1}$ and at 1 MeV, $\lambda(F_e)$ is 0.47 cm$^{-1}$. Thus, for the same counts in the detector, a 60 keV photon beam can detect $\frac{1}{20}^{th}$ the thickness that can be detected by a 1 MeV photon, all other parameters being equal.

It follows that a lightly-loaded container is typically better inspected by the low-energy x-ray components of a radiation beam because $\lambda$ is greater at lower energies. But, a heavily-loaded container must be better inspected by the high-energy x-ray components of a radiation beam. However, the high-energy x-ray components, in turn, increase the ambient radiation dose—the dose of scattered radiation in the surrounding environment.

In accordance with an embodiment of the invention, the energy distribution of an x-ray beam is filtered to simultaneously optimize the penetration of the x-ray beam through a high-density object, as well as the sensitivity of the x-ray beam to a low-density object, while minimizing the ambient radiation dose. The term 'x-ray' is used herein to encompass penetrating radiation generally and, for example, gamma rays are within the scope of the invention.

FIG. 1 is a schematic cross-sectional view of a flying spot x-ray inspection system, i.e., a system in which a scanning pencil beam 20 generated by x-ray radiation source 30 is employed to scan an inspected enclosure such as truck 32. Portions of beam 20 that traverse the inspected enclosure are detected by transmission detector 34, whereas scattered x-rays 36 are detected by one or more scatter detectors 38. Various means are known in the art for mechanically or electronically sweeping a beam of penetrating radiation, including, for example, the rotating chopper wheel 10 depicted in FIG. 1. Electronic scanning is described in detail, for example, in U.S. Pat. No. 6,421,420 which is incorporated herein by reference. In embodiments employing a mechanical rotating chopper wheel, as chopper wheel 10 rotates in the direction of arrow 12, penetrating radiation 14 emitted from the target of X-ray tube 16 passes successively through a plurality (in this case, four) of channels 18. Wheel 10 is fabricated from a material, typically lead, that blocks transmission of x-rays except through channels 18. X-rays 14 emerge from the currently illuminated channel as a pencil beam 20 that is swept across an object undergoing inspection as wheel 10 rotates. The dimensions of the beam 20 typically govern the resolution of a system such as the one depicted.

Aperture stop 44 is a collimating aperture disposed, typically at the distal end of each channel 18 of chopper wheel 10 at the point where beam 20 emerges from the wheel. Aperture 44 may have various shapes, and may be circular or rectangular, and may be more specifically tailored as described in the following section.

Shaped Beam

As alluded to above, the resolution of a flying-spot system is usually limited by the cross-sectional dimensions of x-ray beam 20 at that point in the inspected object where resolution is to be measured. "Tight" beam collimation is a function of both x-ray source target size—the "focal spot" size—and the size of the collimating aperture(s). This is now discussed with reference to FIG. 2.

Since the resolution of a flying-spot system, and thus the ability to resolve small articles and obtain sharp images, depends strongly on collimation of the beam into a well-defined pencil beam, it is advantageous to limit the size of region illuminated by the beam to dimensions no bigger than those of a detection pixel, subject to constraints driven by sampling time and scanning speeds. Collimation of the beam is achieved by means of an aperture defined at the position where a beam exits a channel of the chopper wheel.

Figure 2:
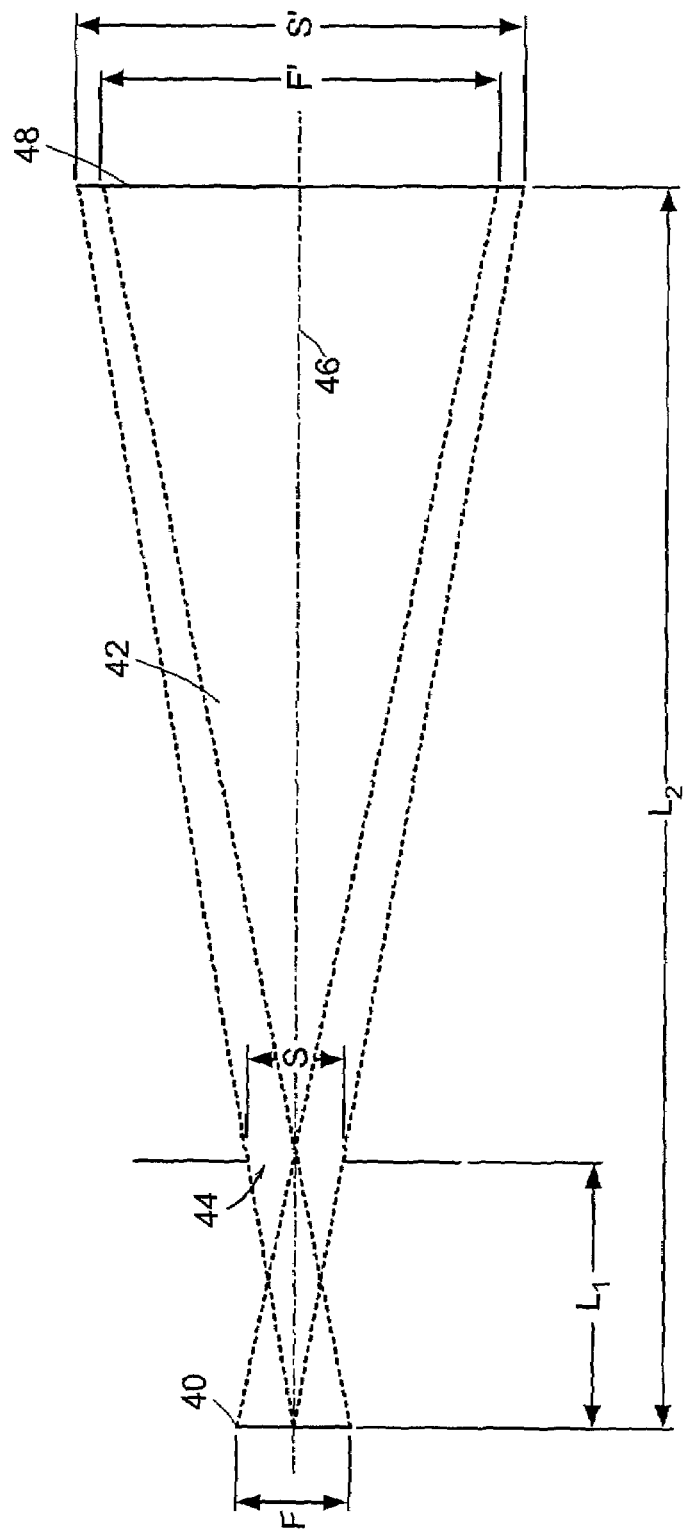
FIG. 2 is a ray trace of x-rays collimated by an aperture in accordance with the invention.

The description of the invention proceeds with reference to the cross-sectional view of the aperture shown in FIG. 2, with the understanding that the actual system may have cylindrical symmetry about central axis 46, but that it typically does not. A characteristic dimension, referred to herein as the "size", of the focal spot at target 40 is designated as F, while the size of aperture stop 44 is designated S. Target 40 and aperture stop 44 are separated by source-to-aperture distance $L_1$.

Object plane 46 refers to a characteristic position within an object being interrogated at which position resolution is to be optimized. F' represents the size of a pinhole image of the focal spot (i.e., the image through an infinitesimal aperture, S→0) at the designated "object distance", $L_2$ referred to the plane of target 40, while S' represents a point projection of the aperture (i.e., from a point source, F→0).

At the object plane distance, $L_2$, $$F' = F(L_2 - L_1)/L_1; \text{ and } S' = S\, L_2/L_1 \qquad \text{(Eqns. 6)}$$

The full beam spread at the object distance is the convolute of F' and S', which has a maximum width equal to the sum of F' and S', and a full-width at half-maximum (FWHM) equal to the larger of F' and S'.

The size of F is typically governed by the choice of x-ray tube (though it might be variable, within the scope of the invention), while $L_1$ and $L_2$ are typically dictated by other system considerations such as the thickness of chopper wheel material required to extinguish the beam, etc., and S is then typically dimensioned to make F' and S' equal, i.e., $$S = F(L_2 - L_1)/L_2 \qquad \text{(Eqn. 7)}$$

The flux of x-rays per unit time in the scanning beam is substantially proportional to the product $F \times S^2$, or, using Eqn. 7, to $F^3$. Ideally, both F' and S' are equal to the pixel size at the object distance; however, this may lead, in view of the small pixel size desired, to an x-ray flux that is too small and thus to a loss of penetration, i.e., to an undesirable limit on how much attenuation may be probed by the interrogating beam. A further limitation is the fact that only a few choices of focal spot F are available if the choice is limited to commercially available x-ray tubes.

Consequently, it is common practice to select and available F and to design S in accordance with Eqn. 7 but subject to the condition of providing adequate flux for the desired application. Thus, optimal resolution is not obtained in cases where the beam attenuation is low, i.e., in paths through the inspected object that are radiographically "thin." Conversely, for "thick" parts of the object (i.e., more highly attenuating of incident penetrating radiation), higher photon flux is required for penetration, even at the expense of resolution.

A further characteristic of x-ray sources typically employed in inspection systems is that they are multispectral. Sources that include x-ray tubes emit a continuum of x-ray energies, with a large number of photons per unit energy at the lower energies of the emitted spectrum, with the spectral power density falling off to zero at the operating voltage of the x-ray tube.

By virtue of this characteristic of the power density spectrum of an x-ray source, the great numbers of lower energy photons dominate the transmission signal (i.e., the flux of photons incident upon detector 34 (shown in FIG. 1) in regions of relatively low x-ray opacity. In accordance with preferred embodiments of the present invention, collimating apertures of graduated attenuation, such as now described with reference to FIG. 3A, are provided that the collimating apertures gradually become more opaque to x-rays with increasing distance from the central axis of the beam.

It is to be understood that, as used herein and in any appended claims, the term "graduated" encompasses within its scope both stepped and continuous variation in attenuation with distance from the central axis. "Graduated" is thus used both in the sense of discrete steps and in the sense in which "grade" is applied to a road.

Moreover, it is to be understood that the manner in which attenuation varies with distance from a fiducial axis may have a specified symmetry, either cylindrical or with respect to inversion through the axis, etc., however the variation need not have any symmetry at all within the scope of the invention as taught herein and as claimed in any appended claims. The fiducial axis characterizing the propagation direction of the beam will be referred to herein, without limitation, as a 'central axis.' Thus, the apertures, for example, may be asymmetrically disposed with respect to a central axis.

Axis 50 designates a central axis of a beam of penetrating radiation. A particular beam spectrum is assumed in the present description, purely for purposes of illustration and without limitation. In particular, a 140 keV x-ray tube is assumed, having a photon distribution as a function of photon energy as depicted by the line designated 70 in FIG. 4. The raw power spectrum of beam intensity of such a beam is as plotted as curve 72, and this is the spectral content of the beam transmitted through the central clear aperture 54 of graduated aperture 52 shown in front view in FIG. 3A.

Figure 4:
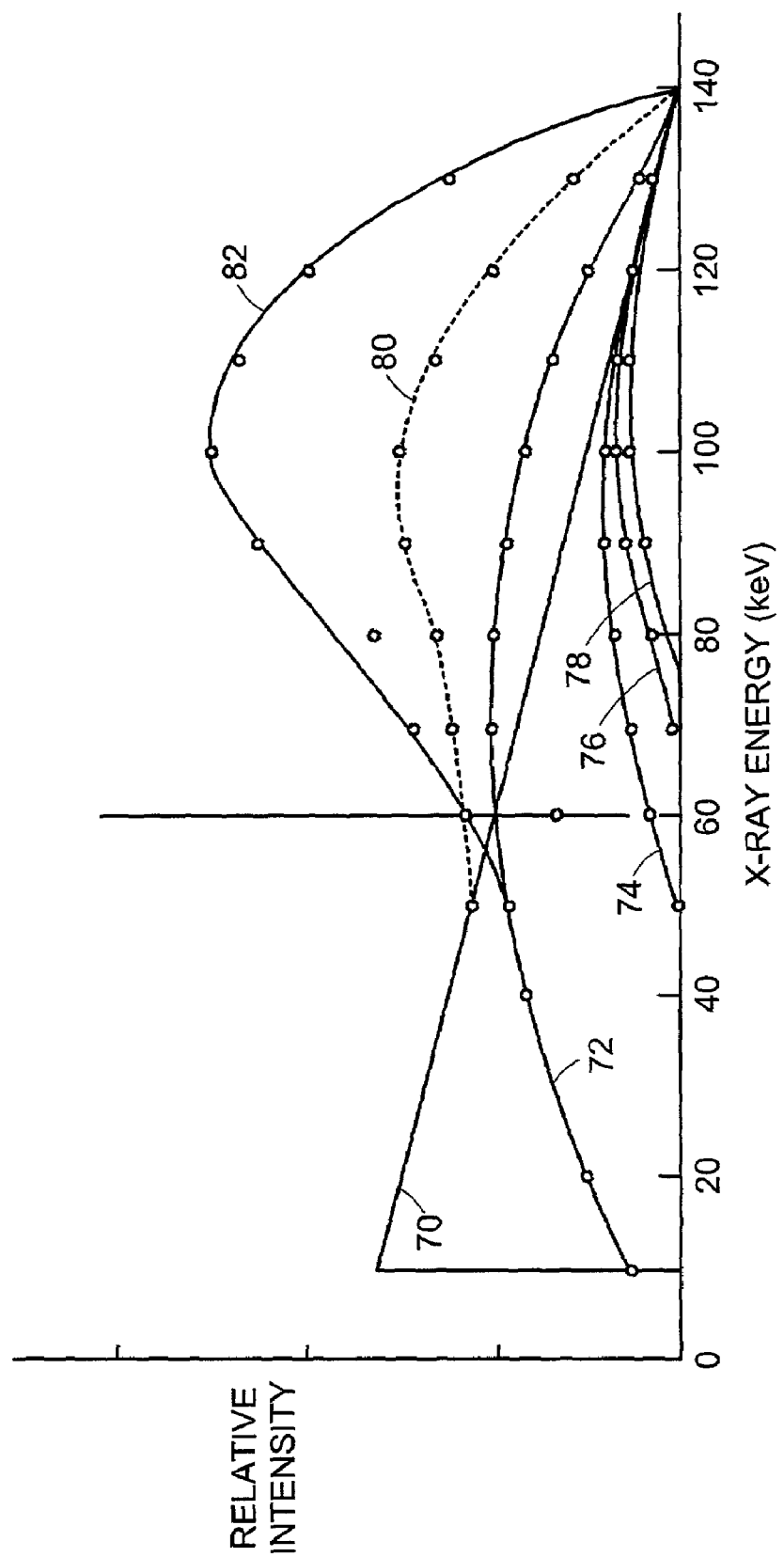
FIG. 4 shows the power spectrum of intensity as a function of photon energy for successive concentric apertures, as shown in FIGS. 3A and 3B, and a specified beam energy spectrum as well as the resultant power spectral distribution through the entire collimator, in accordance with embodiments of the invention.

Solely as an illustrative example of typical aperture sizes, and shaping of the power spectrum of the x-ray beam energies in accordance with the invention, the aperture regions of FIG. 3A are now discussed with further reference to FIG. 4. FIG. 3B shows a side cross section of a graduated aperture such as that shown in FIG. 3A.

In the embodiment of the invention depicted in FIG. 3A, central aperture 54 is fully open and is characterized by an area designated as A. The distribution with x-ray energy of the number of photons in the beam incident from a typical x-ray tube is designated in FIG. 4 by curve 70. This corresponds to the raw spectrum designated by curve 72, accounting for the energy per photon increasing towards the right. Curve 72 thus represents the spectrum of x-ray power transmitted through central aperture 54.

Outside of aperture 54, a frame 56 is disposed having outside length dimensions equal to $\sqrt{3}$ times that of the length dimension of central aperture 54, such that the incremental area of frame 56 is twice that of the central aperture, i.e., 2A. Frame 56 is made of copper of a thickness corresponding to 1 HVL (half-value-layer) of attenuation for 120 keV x-ray photons and central aperture 54 is simply a hole in frame 56. At lower energies, the attenuation is larger, such that the transmission of photons of higher energy is relatively enhanced. The spectrum transmitted through the additional area of frame 56 is depicted by curve 74.

Outside frame 56, a third area 58 is characterized by an attenuating material, such as iron, of thickness corresponding to 2 HVL of attenuation for 120 keV x-ray photons. The third area has outside length dimensions of $\sqrt{7}$ times that of the length dimension of central aperture 54, such that the incremental area of frame 58 is four times that of the central aperture, i.e., 4A. Similarly, an outer frame 60, characterized by an attenuating material, such as iron, of thickness corresponding to 3 HVL of attenuation for 120 keV x-ray photons. The third area has outside length dimensions of $\sqrt{15}$ times that of the length dimension of central aperture 54, such that the incremental area of frame 60 is eight times that of the central aperture, i.e., 8A. Outside area 60, surround 62 is fully attenuating to the incident x-rays, i.e., it may be considered an opaque surround.

Referring to FIG. 4, assuming the raw spectrum designated by curve 72 for the x-ray energy traversing the inner aperture 54, spectra of the relative intensity transmitted through each of the successive framing areas 56, 58, and 60 are depicted as curves 74, 76, and 78, respectively. The composite spectrum, including transmission through each of the regions, is shown as curve 82. As is apparent from the curves of FIG. 4, the spectral peak of the transmitted energy thus increases as a frame is displaced further from the fiducial ('central') axis of the graduated collimator.

It is to be understood that the particular ratios of sides, or, for that matter, the rectangular shape of the apertures, as depicted in FIG. 3A are presented solely by way of illustration and other aspect ratios and aperture shapes are within the scope of the present invention. Indeed, the central aperture 54 need not be clear and may itself be subject to attenuation, and the graduation of attenuation outward from a central axis may be continuous rather than stepped as shown.

Spectral Tailoring

The techniques of spectral tailoring now described may also be referred to as "Shaped Energy™". FIG. 5 is a schematic top view of an exemplary embodiment of an inspection system in accordance with the invention. The system, referenced as system 100, includes generator 110 and collimator 120. Generator 110 generates penetrating radiation and may include, for example, an x-ray tube or a linear accelerator ("LINAC"). The generated x-ray beam typically includes x-ray energies from below approximately 200 keV to above approximately 9 MeV. Collimator 120 forms the generated radiation into a beam 20 of specified cross-section, as appropriate to differing inspection scenarios.

In addition, system 100 includes shaper 130, which shapes the spectrum of beam 20 via section 130a(1), section 130a(2) and section 130b, through which pass distinct spatial segments of beam 20. The term "shaping" as used herein refers to spectral filtering that may be applied differentially with respect to different segments of the beam. Typically, both sections of section 130a, as well as section 130b, attenuate the intensity of the portion of beam 20 that passes through the respective section with specified spectral selectivity. For example, in system 100, section 130b is shown as an opening between section 130a(1) and section 130a(2). Thus, section 130b attenuates the portion of beam 20 that passes through section 130b by a factor of 1. For purposes of discussion herein, an attenuation factor of 1 is the same as no attenuation.

Section 130a(1) and section 130a(2) also attenuate the portion of the beam that passes through each respective section. Typically, section 130a(1) and section 130a(2) are composed of the same material of the same thickness. For example, section 130a(1) and section 130a(2) may be composed of a "heavy" element, for example, an element having an atomic number greater than 23, such as iron, chromium, or lead. However, depending upon the particular application of use for beam 20, section 130a(1) and section 130a(2) may be composed of: (1) the same material, but of different thicknesses; (2) different material, but of the same thickness; or (3) different material of different thicknesses.

In addition, depending upon the particular application of use for beam 20, the configuration of section 130b may be modified. For example, section 130b may be circular in shape. Or, section 130b may be triangular in shape.

System 100 further includes detector 150, which detects shaped beam 20 after shaped beam 20 has passed through object 140. In FIG. 5, object 140 is moving in a direction away from the bottom of the page and toward the top of the page. Detector 150 may be a single detector that efficiently detects both the low-energy x-ray components of shaped beam 20 and the high-energy x-ray components of shaped beam 20. In this embodiment, if the count rate of detector 150 is low enough for pulse counting, then the low-energy and high-energy x-ray components of beam 20 can be distinguished by their pulse heights, a method known in the art. However, if the count rate in detector 150 is too high for pulse counting, the gain in sensitivity for lightly-loaded objects will be less than the gain in sensitivity when more than one detector is used (discussed below). In regard to sensitivity to thickness change in a heavily-loaded object, the sensitivity is the same for one detector as for more than one detector.

When object 140 is a "high-density" object, for example, $\lambda T>1$ at low energies, then the x-ray components that penetrate to detector 150 are substantially the high-energy x-ray components. In turn, when object 140 is a "low-density" object, for example, object 140 is lightly-loaded, then the x-ray components that penetrate to detector 150 are substantially all of the x-ray components of shaped beam 20.

Figure 6A:
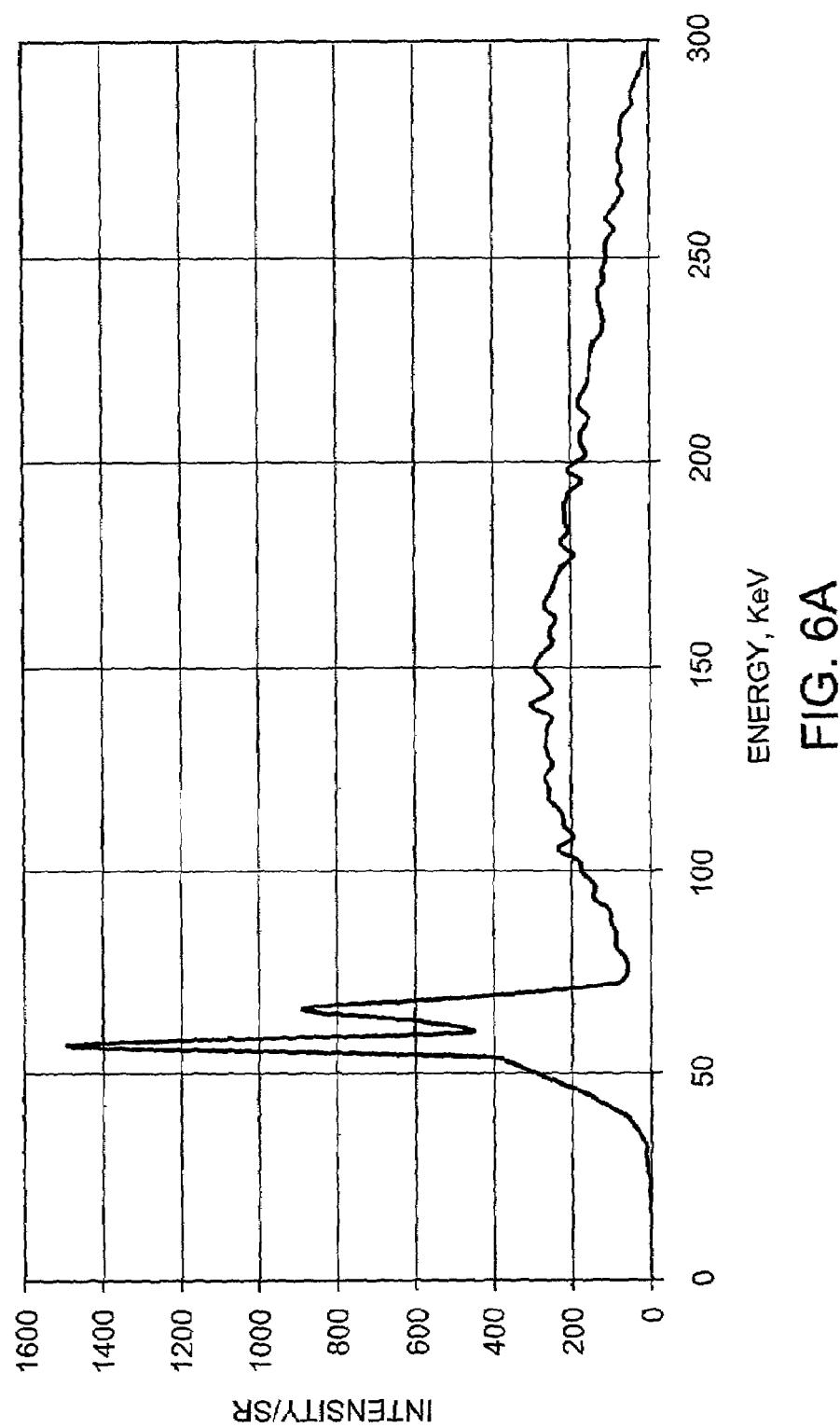
FIGS. 6A–6C show the exemplary energy spectra of a radiation beam that is substantially unattenuated (FIG. 6A), substantially attenuated (FIG. 6B), and shaped in accordance with an exemplary embodiment of the invention (FIG. 6C)
Figure 6B:
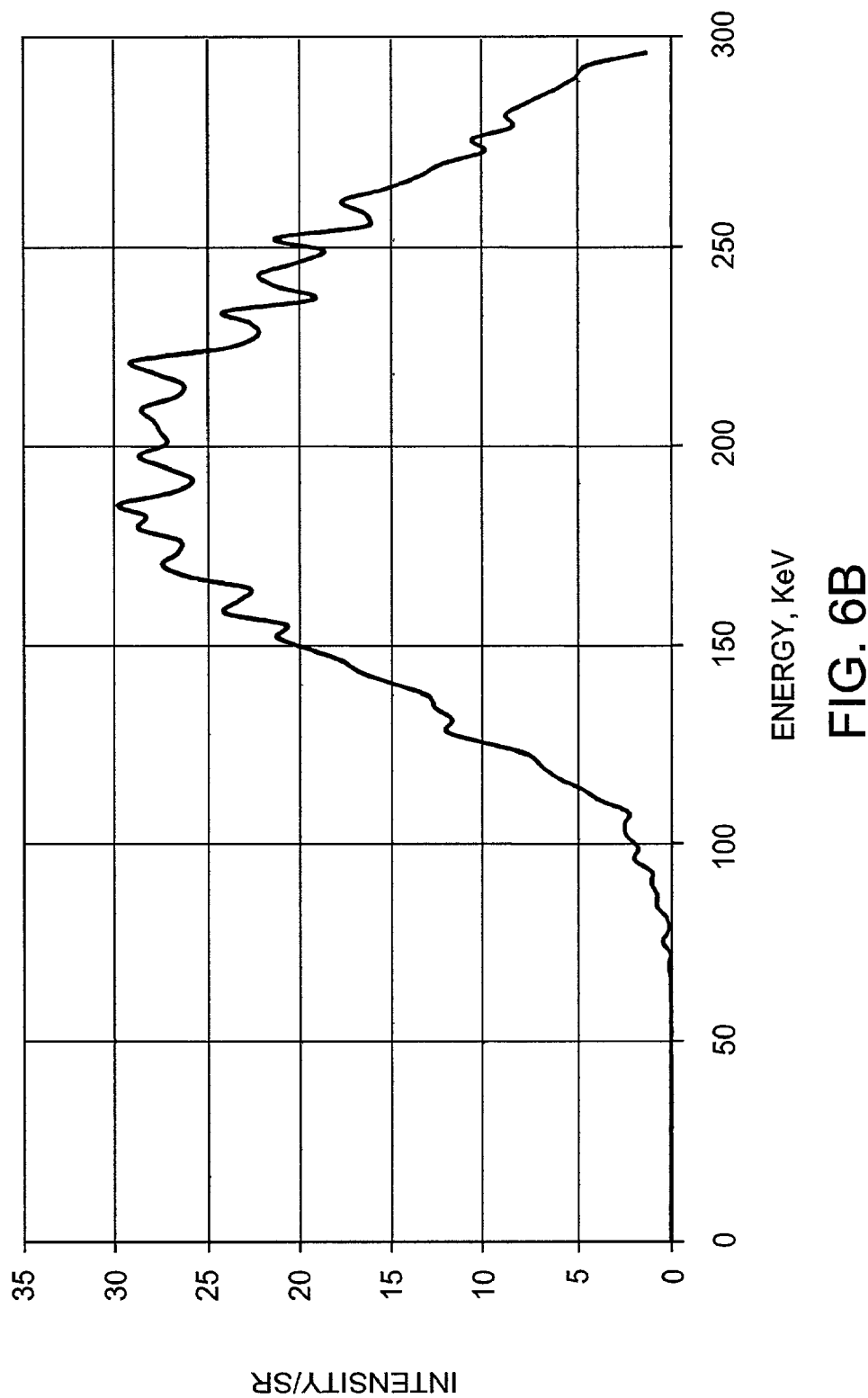
Figure 6C:
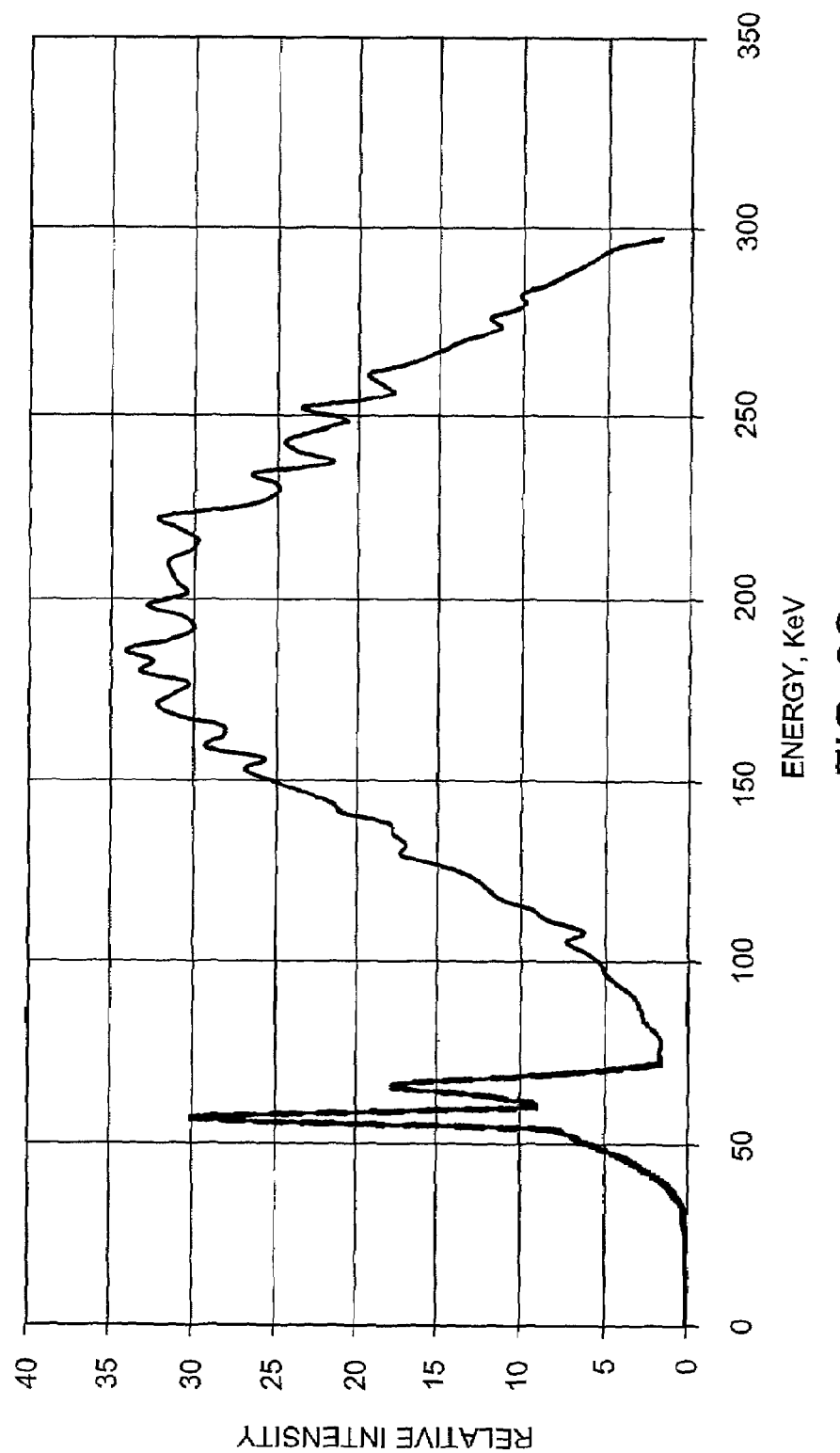

FIGS. 6A–6C show the exemplary energy spectra of a radiation beam that is substantially unattenuated (FIG. 6A), substantially attenuated (FIG. 6B), and shaped in accordance with an exemplary embodiment of the invention (FIG. 6C). In particular, FIG. 6A is an exemplary energy spectrum of a substantially unattenuated 300 keV x-ray beam. As shown, the maximum intensity of the integrated intensity of the energy spectrum is between approximately 60 keV and approximately 75 keV. In contrast, FIG. 6B is an exemplary energy spectrum of a 300 keV x-ray beam that has passed through 2 cm of copper. As shown, the "bulk" of the integrated intensity is between approximately 150 keV and approximately 250 keV. In other words, the 2 cm thick copper has attenuated the intensity of the 300 keV x-ray beam by an attenuation factor, specifically, the 2 cm thick copper has reduced the low-energy x-ray components of the 300 keV x-ray beam by more than a factor of 10,000, and has reduced the high-energy x-ray components of the 300 keV x-ray beam by approximately a factor of 10.

While the reductions differ for the different x-ray energies of the beam, for purposes of discussion herein, these reductions are referred to simply as an energy-dependent attenuation factor. In other words, the use herein of the phrase "attenuation factor" may mean that a particular material reduces different x-ray energies by different factors. Additionally, as used herein and in any appended claims, "modulate" means "to modify a characteristic of," whether such modulation is a function of space, energy, or time.

FIG. 6C is an exemplary energy spectrum of a radiation beam shaped in accordance with an exemplary embodiment of the invention, in particular, with reference to the exemplary embodiment shown in FIG. 5. Specifically, FIG. 6C shows the spectrum of a 300 keV x-ray beam, generated by generator 110, that has passed through shaper 130, in which section 130a(1) and section 130a(2) of shaper 130 are composed of copper that is 2 cm in thickness, and section 130b of shaper 130 allows an areal fraction of approximately 2% of the 300 keV x-ray beam to pass through section 130b without attenuation. As shown, the "bulk" of the intensity of the energy spectrum is between approximately 60 keV and approximately 75 keV and between approximately 150 keV and approximately 250 keV. In other words, the 'shaped' spectrum is the sum of approximately 2% of the energy spectrum shown in FIG. 6A and approximately 100% of the energy spectrum shown in FIG. 6B. Accordingly, the 'shaped' spectrum contains sufficient low-energy x-ray components to inspect a low-density object 140, for example, object 140 has an absorption equivalent to 1 cm of iron, and sufficient high-energy x-ray components to inspect a high-density object 140, for example, object 140 has an absorption equivalent to 10 cm of iron, while substantially reducing the ambient radiation dose.

Figure 7:
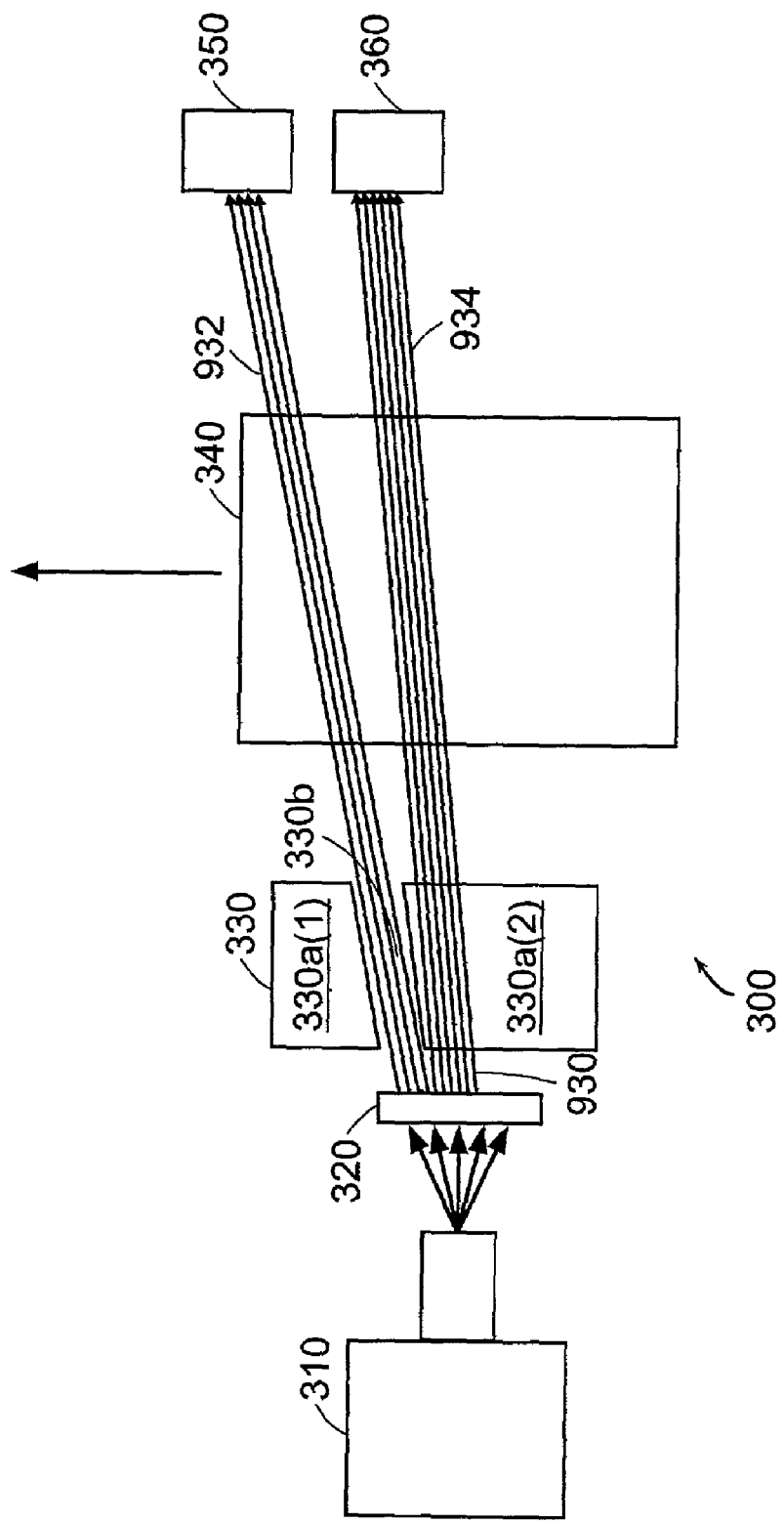
FIG. 7 is a schematic top view of an exemplary embodiment of an inspection system in accordance with the invention using a shaper to attenuate portions of a radiation beam using different attenuation factors, as well as separate the radiation beam, and two detectors to detect the separate, shaped beams.

FIG. 7 is a schematic top view of another exemplary embodiment of an inspection system in accordance with the invention. As in the exemplary embodiment shown in FIG. 5, the system, referenced as system 300, includes a generator 310 and a collimator 320. In this exemplary embodiment, however, the shaper 330, modulates beam 930 by both attenuating the intensity of at least a portion of the beam, beam 930, and separating beam 930 into a first beam 932 and a second beam 934. In particular, section 330a(1), section 330a(2), and section 330b attenuate the intensity of the portion of beam 930 that passes through the respective sections. Thus, the first beam 932, which passes through section 330b, is attenuated in accordance with a first attenuation factor (which, for this exemplary embodiment, equals 1), and the second beam 934, which passes through section 330a(2), is attenuated in accordance with a second attenuation factor.

Depending upon the particular application of use for beam 930, beam 930 may pass through section 330a(1) and section 330b, rather than section 330a(2) and section 330b. Or, in the alternative, beam 930 may pass through all three sections of shaper 330. In addition, as discussed above, the configuration of section 330b may be modified. Moreover, as discussed above, section 330a(1) and section 330a(2) may be composed of: (1) the same material of the same thickness; (2) the same material, but of different thicknesses; (3) different material, but of the same thickness; or (4) different material of different thicknesses. Of course, description of the system in terms of three attenuating sections is for the purpose of example only and any number of attenuating sections may be employed within the scope of the invention.

System 300 further includes two or more detectors, shown as detector 350 and detector 360. Detector 350 detects the first beam 932 of shaped beam 930 after the first beam has passed through object 340. As with object 140 in FIG. 5, object 340 is moving in a direction away from the bottom of the page and toward the top of the page. Detector 360 detects the second beam 934 of shaped beam 930 after the second beam has passed through object 340. In one exemplary embodiment, the first beam 932 of beam 930 may include, for example, the low-energy x-ray components of beam 930. In this embodiment, detector 350 might be designed to be primarily sensitive to the low-energy x-ray components of beam 930. Similarly, the second beam may include, for example, the high-energy x-ray components of beam 930. In this embodiment, detector 360 might be designed to be primarily sensitive to the high-energy x-ray components of beam 930.

Figure 8:
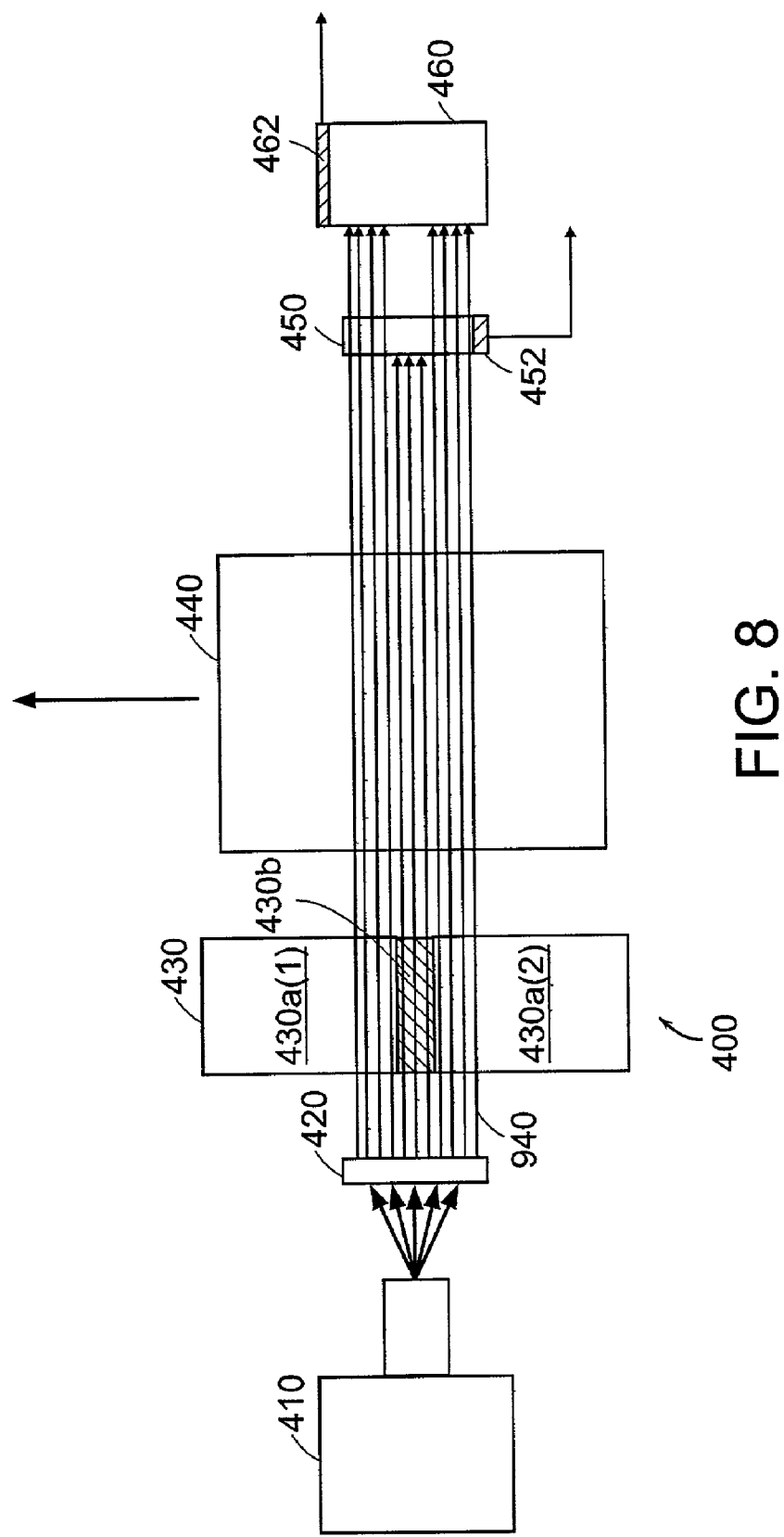
FIG. 8 is a schematic top view of an exemplary embodiment of an inspection system in accordance with the invention using a shaper to attenuate portions of a radiation beam using different attenuation factors and two detectors to detect the various photon energies of the shaped beam.

FIG. 8 is a schematic top view of still another exemplary embodiment of an inspection system in accordance with the invention. As in the exemplary embodiment shown in FIG. 5, the system, referenced as system 400, includes a generator 410, a collimator 420, and two detectors 450 and 460. In this exemplary embodiment, however, detector 450 and detector 460 are in tandem. In addition, the shaper, shaper 430, modulates the beam, beam 940, by attenuating the intensity of beam 940, but not by separating beam 940 into a first beam and a second beam. Rather, as with shaper 130 of FIG. 5, shaper 430 attenuates the intensity of an areal portion of beam 940 in accordance with a first attenuation factor, and attenuates the intensity of the remaining portion of beam 940 in accordance with a second attenuation factor.

Moreover, in this exemplary embodiment, section 430b of shaper 430 is composed of some material of some thickness. Thus, unlike section 130b and section 330b, section 430b attenuates the portion of beam 940 in accordance with an attenuation factor that is not equal to 1. Section 430b may be composed of the same material, but of a different thickness, than section 430a(1) or section 430a(2). Or, section 430b may be composed of a different material, but of the same thickness, as section 430a(1) or section 430a(2). Or, section 430b may be composed of a different material of different thickness than section 430a(1) or section 430(a)(2). In turn, as discussed above, section 430a(1) and section 430a(2) may be composed of: (1) the same material of the same thickness; (2) the same material, but of different thicknesses; (3) different material, but of the same thickness; or (4) different material of different thicknesses. Moreover, as discussed above, the configuration of section 430b may be modified.

As discussed, detector 450 and detector 460 are in tandem. Typically, detector 450 is optically isolated from detector 460, to stop scintillation from detector 460 being detected in detector 450. This may be achieved, for example, by painting the back side of detector 450 (the side facing detector 460) with black paint. In one exemplary embodiment, detector 450 might be designed to be primarily sensitive to the low x-ray energy components of beam 940 and detector 460 might be designed to be primarily sensitive to the high-energy components of beam 940. For example, detector 450 may be a 0.6 mm thick detector of CsI scintillator and detector 460 may be a 1 cm thick detector of CsI scintillator. In this embodiment, detector 450 has photo-diode 452 to detect the photons generated in its scintillator, and detector 460 has photo-diode 462 to detect the photons generated in its scintillator. The signal current from photo-diode 452 measures the low-energy x-ray components of shaped beam 940, and the signal current from photo-diode 462 measures the high-energy x-ray components of shaped beam 940.

In another exemplary embodiment with detector 350 and detector 360 arranged in tandem, detector 350 might be designed to be efficient for detecting the low-energy x-ray components of beam 930 and inefficient for stopping the high-energy x-ray components of beam 930. In turn, detector 360 might be designed to be highly efficient for stopping all energy components of beam 930 but, because detector 350 absorbs the low-energy x-ray components of beam 930, detector 360 need only detect the high-energy x-ray components of beam 930.

Mobile Inspection System with Spatially and Spectrally Tailored Beams

Figure 9A:
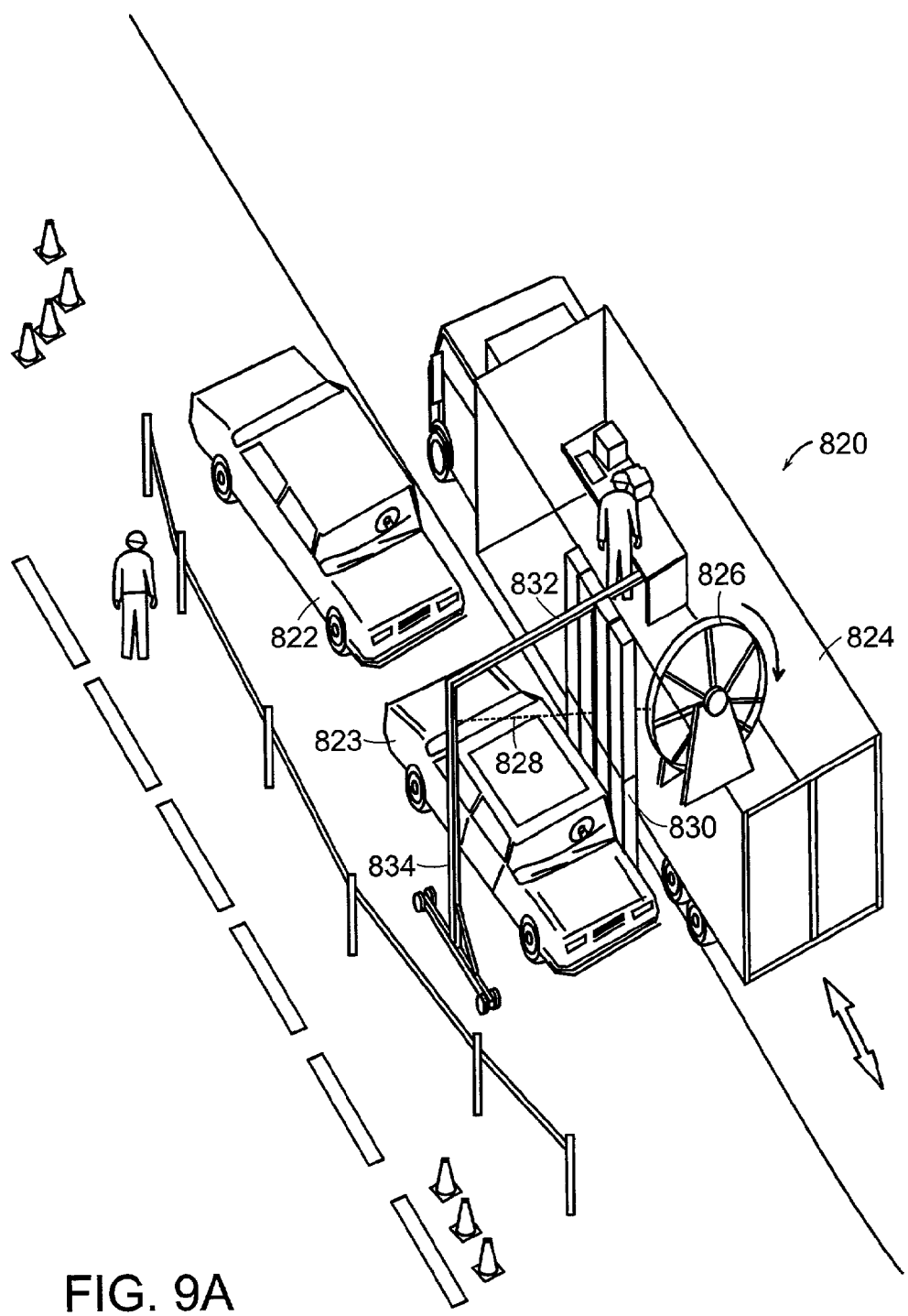
FIG. 9A is a perspective view of a device for inspecting a large container with penetrating radiation in accordance with a preferred embodiment of the invention.

In other embodiments of the present invention, a cargo container inspection device uses flying-spot x-ray imaging (either in transmission, backscatter, or both) as practiced from a mobile inspection vehicle employing spatially and spectrally tailored beams as described above. Referring now to FIG. 9A, a perspective view is shown of a cargo container inspection system, designated generally by numeral 820, in accordance with a preferred embodiment of the invention. Further description of the rudiments of a mobile inspection system are provided in U.S. Pat. No. 5,764,683 (Swift et al.), issued Jun. 9, 1998, which is incorporated herein by reference.

Figure 9B:
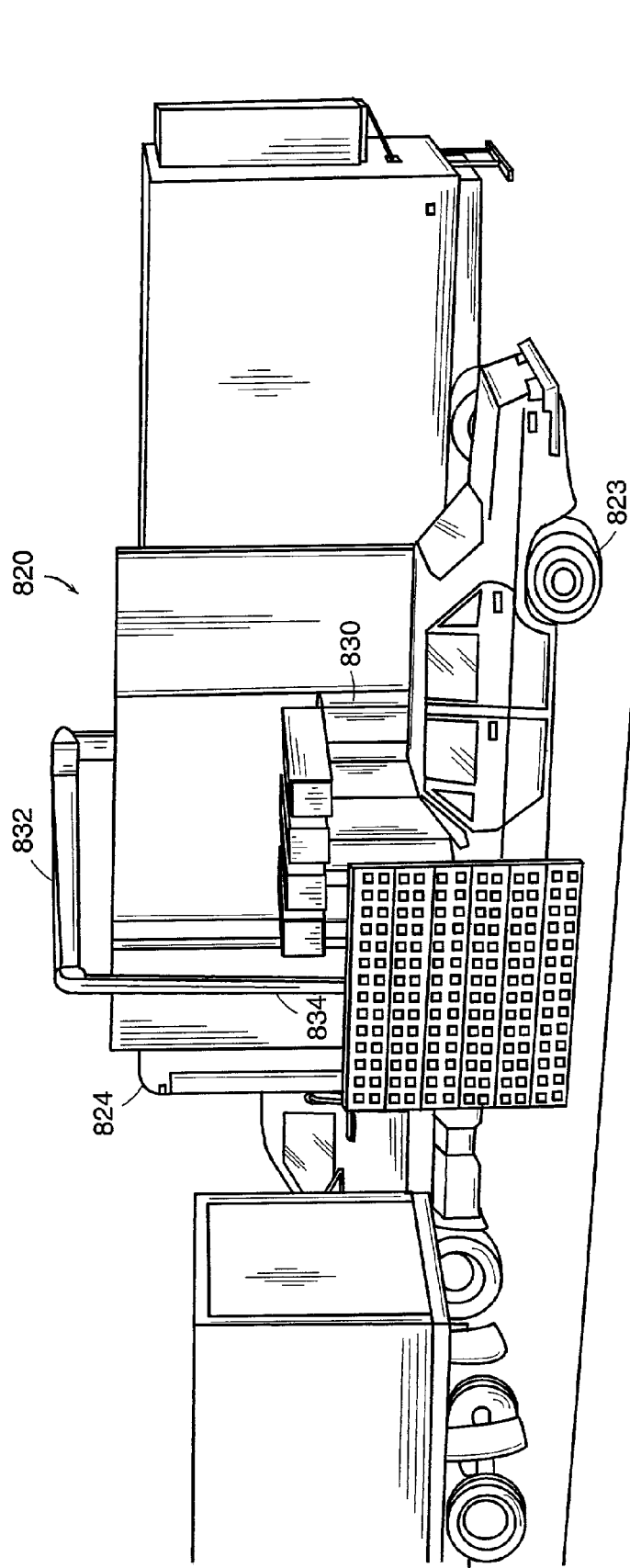
FIG. 9B is a side view of a further embodiment of a device for inspecting a large container with penetrating radiation in accordance with the invention.

In FIG. 9A, cargo container inspection system 820 is shown deployed for inspection of passenger cars 822 and 823. FIG. 9B shows a preferred embodiment of the invention.

With reference to FIGS. 9A and 9B, a truck 824, typically 35' long×8' wide×10'6" high, houses and supports the x-ray inspection equipment, ancillary support and analysis systems, and a hydraulic slow-speed drive mechanism to provide the scan motion. Truck 824 serves as both the platform on which the mobile system is transported to its intended operating site, and a bi-directional translation stage, otherwise referred to herein as a "bed," to produce the relative motion required during a scan. Chopper 826 is used, in accordance with flying spot generation discussed above, in reference to FIGS. 1–8, to scan beam 828 of penetrating radiation recursively in a vertical direction. Radiation scattered by the contents of the cargo container, shown here as passenger car 823, is detected by x-ray backscatter detectors 830. Boom 832 allows beam stop 834 to intercept beam 828 as it emerges from the distal side of the scanned cargo container. Beam stop 834 is also referred to as a "beam catcher." In addition or alternatively to beam stop 834, an x-ray transmission detector, designated by numeral 34 in FIG. 1, may be mounted in opposition to beam 828. It is to be understood that the positions of the source 840 and the transmission detector 34 may be reversed, and that source 840 may be carried on the side of the cargo container that is distal to truck 824. It is, furthermore, to be understood that the term 'source' as used herein and in any appended claims, and as designated by numeral 840 in the drawings, refers to the entirety of the apparatus used to generate beam 828, and may have internal components that include, without limitation, apertures, choppers, collimators, etc.

Figure 10:
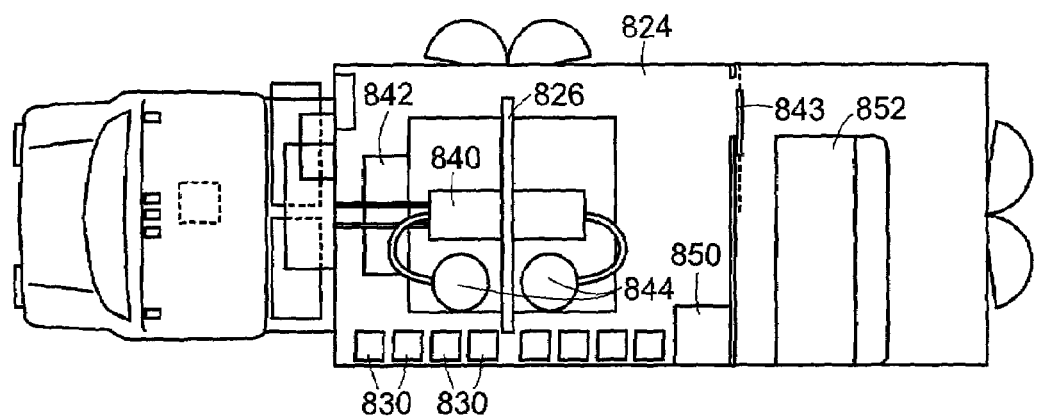
FIG. 10 is a top schematic view of the layout of the system shown in FIG. 9B, as configured for transport.
Figure 11:
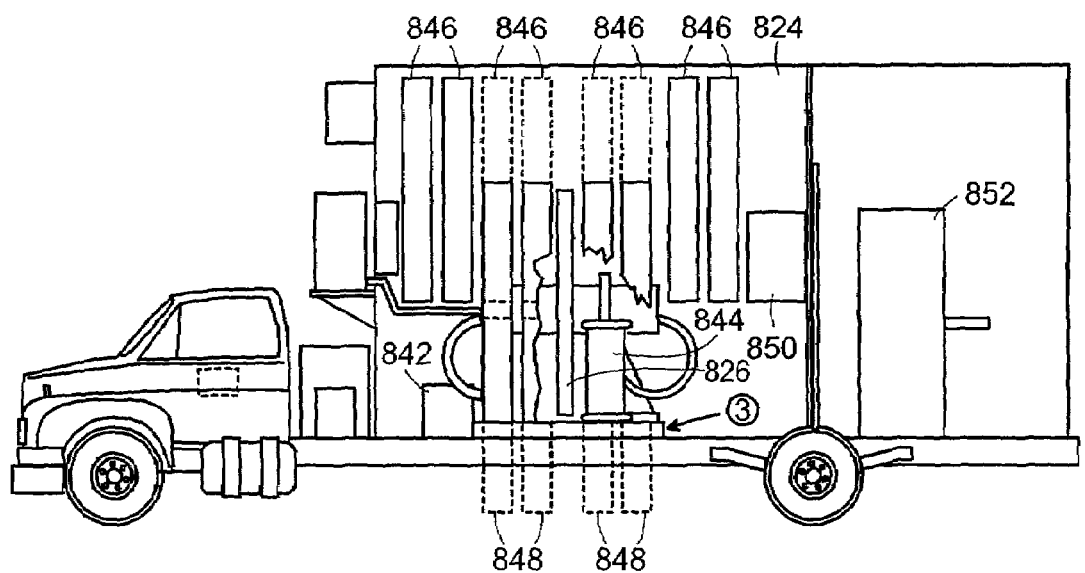
FIG. 11 is a side elevation schematic view of the layout of the system shown in FIG. 9B.

Referring now to FIG. 10, a top schematic view of the layout of the system shown in FIG. 9B, is depicted as configured for transport. FIG. 11 is the corresponding side elevation, additionally showing the detectors in one of two available deployed positions. The modular components comprising the cargo container inspection system are: the penetrating radiation source assembly 840; x-ray high voltage generating subsystem including high voltage power supply 842 and high voltage tanks 844; backscatter detector modules 830, comprised of an upper bank 846 of detectors and a lower bank 848 of detectors; detector electronics module 850; and operator's console 852. The dashed position of upper backscatter detector banks 846 indicate the position for inspection of cargo containers. The x-ray source 840, high-voltage power supply 842, and positive and negative high-voltage tanks 844, are all in accordance with ordinary practice in the art of x-ray generation. In a preferred embodiment of the invention, a 450 kV x-ray tube is employed.

Figure 12A:
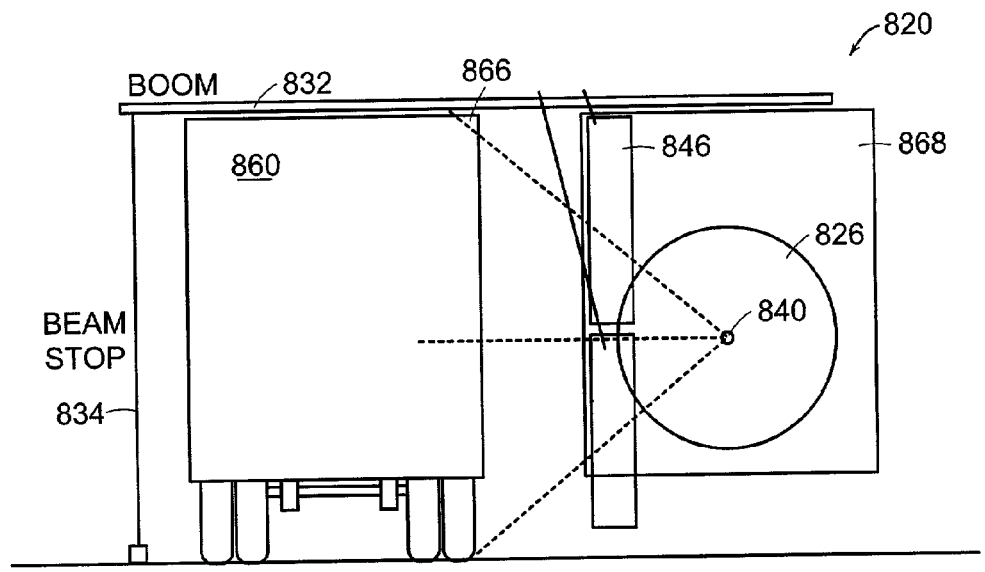
Figure 12B:
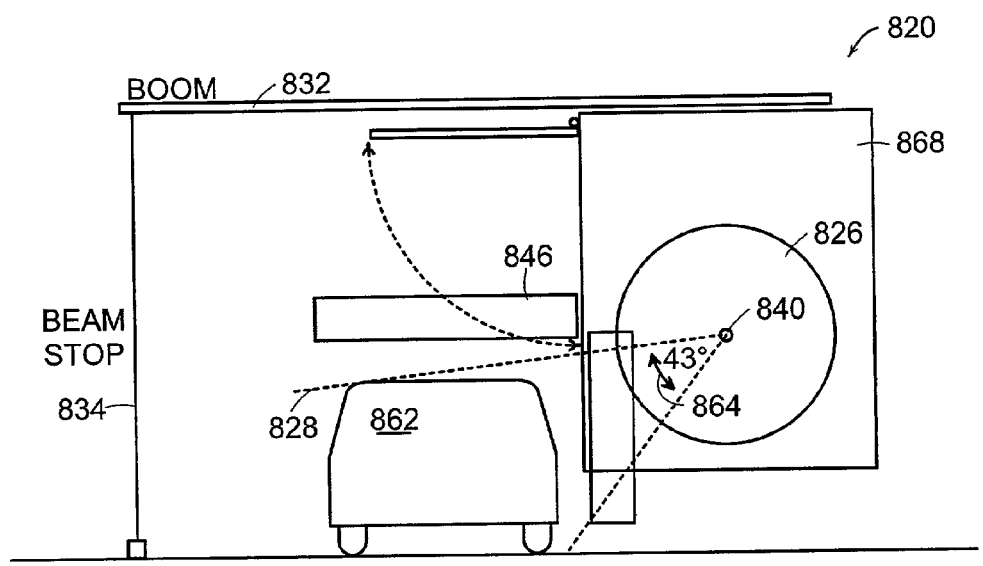
FIG. 12B shows the cargo container inspection system of FIG. 9B, as deployed for inspection of a car.

FIG. 12A shows a cargo container inspection system 820, in accordance with a preferred embodiment of the invention, as deployed for inspection of a full-sized tractor-trailer 860 while FIG. 12B shows the same cargo container inspection system 820 deployed for inspection of a passenger van 862. The angle of elevation 864 of the 43° scanning beam can be changed depending upon the application. For optimum versatility, the range of limiting angles extends from at least 55° below horizontal to 55° above horizontal. This corresponds to an angular adjustment of the source axis from −33.5° to +33.5°.

Operationally, one side of a large truck 860 (up to 14' height), as depicted in FIG. 12A, can be completely covered in three passes; however, in many cases, satisfactory coverage can be achieved in two passes, such as through the use, for example, of an x-ray source having a 90-degree opening angle. The system operators must choose between doing a third pass or tolerating a small amount of corner cutoff 866, in which case, higher inspection throughput can be achieved. Since the scanning system is bi-directional, alternate passes can be in the forward and reverse directions.

Operationally, as well, one-side of passenger cars and small trucks may be scanned in a single pass of the system. Depending upon the situation, it may be necessary to scan the opposite side as well. The upper set 846 of backscatter detectors can be deployed over the top of smaller vehicles as shown in FIG. 12B, substantially improving the scatter collection efficiency and producing higher quality images. Backscatter detector modules 846 and 848, two are typically 6' long and 1' wide, and each typically comprises four segments.

In a preferred embodiment of the invention, the cargo container inspection system has two scan-speed modes: nominally 3 inches/sec and 6 inches/sec. The faster speed results in higher throughput, the slower mode—higher image quality. In accordance with one embodiment of the invention, image data in either mode is acquired into a 1024×4096×12 bit image memory and displayed onto a 1024×1024 high-resolution display via a continuously-adjustable 12-bit-to-8-bit look-up table. Additional displays can be provided to allow simultaneous viewing of more than one image, or, alternatively, images may be superposed or combined, as known to persons skilled in the art.

Backscatter detectors are mounted to allow efficient collection of scattered radiation from close to the road surface, all the way to the roof of the inspected container. A motorized mechanism enables the upper set of detectors to be deployed over a small vehicle, as shown in FIG. 12B, though other means of deployment are readily apparent to persons skilled in the mechanical arts and are within the scope of the invention.

The operator's console 852 (shown in FIG. 11), provides for the console operator to control the x-ray system and display images. Various display monitors may be provided. One preferred embodiment has an upper display for transmission images, and a lower display for the corresponding backscatter image. Similarly, various display functions may be provided:

Zoom, pan and scroll—Joystick controls allow the operator to display any part of the image at 2× and 4× magnifications.

Continuous density expand—This contrast-enhancing feature allows the operator to display any contiguous subset of the 12-bits (4096 digital intensity levels) of image data over the full black-to-white range of gray levels on the display monitors. The implementation is through a set of 10 pre-set push buttons, along with a trackball for fine-tuning.

Edge enhancement—A mathematical algorithm sharpens the image and extends the effective dynamic range of the display for faster and easier image analysis.

Reverse video—Operators may select between positive (black-on-white) or negative (white-on-black) image display, depending on personal preference.

Image archiving—Operators may "mark and annotate" the images from the console keyboard, and store them on optical disk for future recall.

Truck 824 containing cargo container inspection system 820 is fitted with a custom-built box (or truck body) 868 (shown in FIGS. 12A and 12B) specified to accommodate the imaging equipment, and to provide support structures, environmental control, and electrical power distribution.

Truck 824 is provided with both front- and rear-wheel drive: Standard rear-wheel drive from the truck's engine is used for normal over-the-road travel. An alternative drive mode is powered by a low-RPM hydraulic motor to obtain the very low speeds employed for the scan. The two drives are connected via a switchable gearbox to preclude the possibility of having both active at the same time. The hydraulic motor controls, including speed selection, drive direction, and motion start/stop, are located in the cab of the truck under the control of the driver. As an additional safety feature, actuation of the truck's brake will automatically cause disengagement of the hydraulic clutch. A similar arrangement using a hydraulically-powered front or rear wheel drive is known in the art for other special applications requiring very slow vehicle motion.

Deployable beam stop 834 is employed to assure compliance with FDA radiation safety requirements. However, the output radiation of the system is so low that the health and safety requirements for low radiation levels is met only a few feet away from the source even if no beam stop is used. Beam stop 834 uses a dense shielding material such as lead that is deployed from the end of a boom 832 that extends about 14' from the side of truck 824 at the location of the x-ray beam 828. Generation of x-rays is prevented by interlock circuits unless boom 832 and beam stop 834 are properly deployed.

To stow the beam stop for road travel, the beam stop is retracted into the hollow boom 832. Boom 832 is then rotated parallel to the truck axis and lowered into a cradle in truck box 868.

The scan motion is exceedingly slow—typically, ⅓ to ⅙ of a mile per hour. An audible alarm is actuated whenever the scan drive mechanism is engaged for motion in either direction. Since this motion also coincides with x-ray generation, the audible warning also provides an "X-RAYS ON" warning. The x-ray high voltage power supply 842 is interlocked so that it cannot be energized unless both chopper wheel 826 is up to speed and truck 824 is in motion. This additional safety precaution ensures that the scanning beam will not be stationary over any one region of space for a long time, thus ensuring low delivered dose.

Operation will be described as it applies to the inspection of one or more passenger cars; scanning of large vehicles will be similar, except that the upper detectors do not need to be swung outboard in this case. It will also be assumed that the system will first be set up, and that vehicles to be scanned will then be brought to it. An alternative whereby the system is deployed beside parked vehicles or containers calls for a minor variation of procedures.

Upon arrival at the intended inspection site, the operators will first assure that the site is suitable: i.e., that there is a sufficient space available for system operation and that operating space can reasonably be secured for safe operations. They will then position the truck at the starting position for the first scan, assuring that there is sufficient room to move the truck ahead for the required scan distance, usually about 65 feet. (Scans will normally alternate, forward and back; it is also possible to scan sequentially in the forward direction only, to scan a continuous line of parked vehicles for example, provided that the necessary space is free.) Once positioned, the on-board generator is started to provide power for system operation, lighting, and a cooling unit. Operator's console 852 is powered up at this time.

The operators then manually deploy the backscatter detectors and the beam stop using a motorized mechanism provided for that purpose. Only the upper set of detectors 846 deploy, as shown in FIG. 12B. The beam stop is deployed by rotating the boom into a position orthogonal to the truck, and then lowering the beam stop out of the boom to its preset limit. This action closes an interlock circuit that is required before x-ray generation is possible. An x-ray tube warm-up sequence, if necessary, is then initiated from operator console 852.

Following warmup, the physical configuration of the system setup is completed by rotating the x-ray beam angle to the direction (elevation) required for the intended scan operations. This is done by a manually-actuated electric motor, and with the aid of an indicator gauge to assist in setting the desired scan elevation. Scanning operations can then commence.

Scan operations are simple and straightforward. One or more vehicles are directed to positions along the scan path (up to 65 feet of total vehicle length may be imaged in a single scan) and the drivers and passengers exit the vehicles.

Using menu-driven software, the system's computer is readied for image acquisition. This places the computer and data acquisition electronics into a status wherein c-rays will be initiated and image acquisition started upon receipt of a "scan" command initiated by the system's slow-speed drive controls. The computer also transmits a "ready" status signal to the scan drive control located next to the driver of truck 824.

The driver sets the desired scan speed and direction at the scan drive control. After the "ready" status is received from the computer, the driver starts the scan by pushing a "start" button and releasing the truck brakes. "Start" initiates motion via the slow-speed drive. The driver has continuous control over the truck. He is responsible for steering, and may stop the truck at any time by actuating the brake. Otherwise, the scan will stop automatically after a full data set has been acquired by the computer (and the "ready" status is removed).

As soon as the truck is in motion, a "scan" signal is sent to the computer. The computer then triggers the x-ray generator to ramp up to its pre-set operating conditions, and upon confirmation that they have been reached (about 5 seconds later) it starts data acquisition. Data acquisition continues until either the "scan" command is interrupted or the image memory is full.

To break the system down for transportation, electronic systems are shut down and the beam stop and detector mechanisms are retracted and secured for travel. The hydraulic drive is disengaged and its power shut off. The generator is switched off. In a further embodiment, preferred in various applications, the intensity of the transmitted x-ray beam may be measured by a single, elongated transmission detector located on the opposite side of the inspected object from the x-ray source and carefully aligned with the plane of the x-ray beam. The detector is designed to accept and respond to x-rays striking anywhere along the length of its linear entrance slit. The detector is oriented so that the flying-spot beam sweeps repetitively from end-to-end along the slit while truck 824 moves past the inspected object. The detected signal is amplified, integrated, sampled and digitized into an image memory over many sequential, short time intervals during each sweep of the pencil beam. Each such digitized sample forms one pixel of the final image, and the series of samples acquired during one sweep of the beam constitutes one line of image data—typically 1024 samples per line. A complete image frame is constructed by acquiring successive lines as the object is moved through the scan plane.

In the flying beam mode, the positional image information is acquired by correlating the instantaneous detector output with the position of the flying-spot beam at that instant of time. In a corresponding "fanbeam" system an entire line is illuminated at once and individual pixels along the line are acquired either by a large number of discrete detectors arranged along the line, or one or more detectors with positional sensitivity.

The transmission detector may comprise scintillators optically coupled to photomultiplier tubes. This method is more efficient and exhibits less electronic noise than a method using a photodiode array. The resulting improvement in signal/noise allows equivalent images to be made at lower doses and with lower beam energies.

It is to be understood that, within the scope of the invention, the source of penetrating radiation may lie on the opposite side of the inspected object as the mobile platform 824.

Relocatable Inspection System with Spatially and Spectrally Tailored Beams

In other embodiments of the present invention, a cargo container inspection device uses flying-spot x-ray imaging (in transmission, backscatter, or both) with spatially and spectrally tailored beams as described above, and backscatter imaging technologies, where inspection is practiced from two segments disposed astride an inspected item such as a cargo container or a truck.

Figure 13:
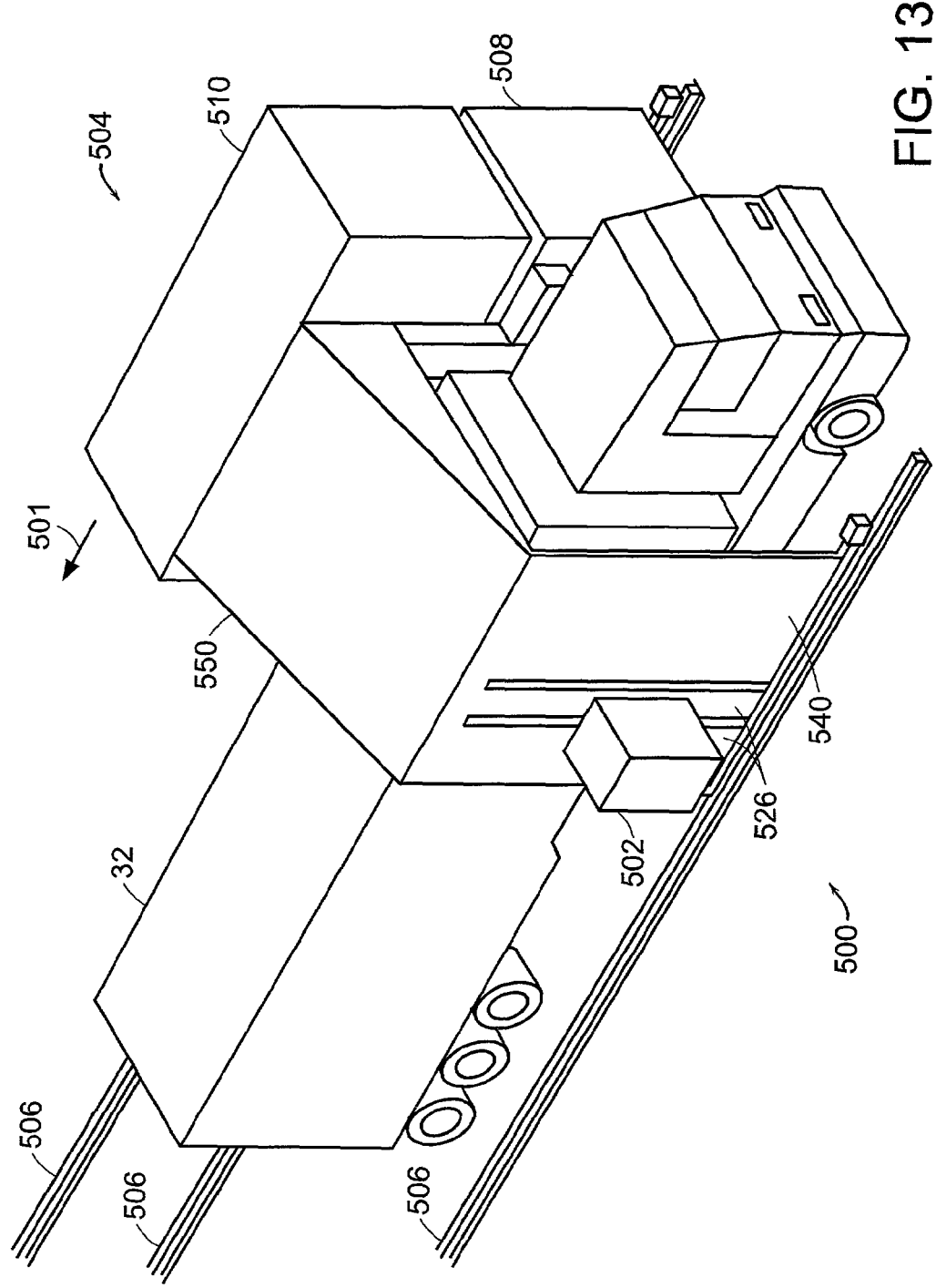
FIG. 13 is a perspective view of a system for inspecting a large container with penetrating radiation in accordance with a preferred embodiment of the invention.

Referring now to FIG. 13, a perspective view is shown of a cargo container inspection system, designated generally by numeral 500, in which an enclosure 32, shown here as the trailer of a truck, is inspected while at rest. One or more sources 502 provide one or more beams of penetrating radiation that are incident at points on the surface of enclosure 32 that vary as source 502 moves with respect to the enclosure. In the embodiment shown in FIG. 13, an x-ray inspection module 504 is driven along a set of parallel tracks 506 and thus traverses cargo enclosure 32. Inspection module 504 includes a lower module 508 containing a source of x-ray irradiation, typically a LINAC with spectral shaping of a beam as described above, and an upper module 510 in which an operator's console is located for control of the inspection system during the course of inspection. Modules 508 and 510 are preferably cargo containers themselves for ease of transportation to and from and particular inspection site.

In accordance with embodiments of the present invention, independent x-ray generators are used to provide sources of penetrating radiation for transmission and scatter images. One or more x-ray generators may be used for each modality. Referring to FIG. 14, a top view of a cargo container 32 being examined by two backscatter x-rays systems 512 and 514, one on either side of container 32, and a spectrally shaped transmission system 516. It is to be understood that the horizontal disposition of each of systems 512, 514 and 516, is a matter of descriptive convenience and that, within the scope of the present invention, any of the systems may be at another angle, such as vertical, with respect to the ground.

Describing, first, backscatter x-rays systems 512 and 514, x-ray beam 520 is emitted by an x-ray source 522 of one of various sorts known to persons skilled in the art. Beam 520 may also be comprised of other forms of penetrating radiation and may be monoenergetic or multienergetic, or, additionally, of varying spectral characteristics. Backscatter x-ray beam 520 is typically generated by a DC voltage applied to the anode of an x-ray tube 522 so that beam 520 is typically continuous. However, a beam 520 of other temporal characteristics is within the scope of the invention. Beam 520 has a prescribed cross sectional profile, typically that of a flying spot or pencil beam. Beam 520 will be referred to in the present description, without limitation, as an x-ray beam, and also, without limitation, as a pencil beam. In a preferred embodiment of the invention, a scanned pencil beam, whose position and cross section is well known at every point in time, is used. The cross section of the pencil beam defines the spatial resolution of the images. Typical pencil beam sizes are a few mm in diameter at a distance of a meter from the beam defining collimation; that is, an angular spread in the beam of <5 milliradians.

Backscatter beam 520 is typically characterized by x-ray energies in the range below 450 keV, and even below 220 keV, so that detected backscatter has a component significantly dependent on the composition of the scattering material Penetrating radiation scattered by an object 527 within enclosure 32 is detected by one or more x-ray detectors 526 and 528 (shown also in FIG. 13). X-ray detectors 528 may be disposed more distantly from x-ray beam 520 than other detectors 526 detect x-rays singly scattered only from more distant objects 527 whereas any scattering incident on outer detector 528 from a near-field object 530 must be due to multiple scattering of the x-ray radiation within the near-field object and is thereby sharply attenuated. Consequently, inner detectors 526 are preferentially more sensitive to near-field objects 530, while outer detectors 528 are preferentially more sensitive to far-field objects 527. Since beam 520 is typically a pencil beam, i.e., a beam having a narrow angular extent, typically on the order of 1°, the source of detected scattering may be localized both with respect to depth and with respect to lateral position. In order to obtain greater spatial resolution of the source of scattered radiation, collimators 532 may be employed, as known to persons skilled in the x-ray art, for narrowing the field of view of segments of detector 528. Backscatter system 514, with source 515 and detectors 529 is disposed on the same side of enclosure 32 as transmission source 536.

Transmission system 516 is now described. X-ray beam 534 is produced by source 536 which is typically a high energy source of penetrating radiation such as a LINAC for example. In certain embodiments of the invention, beam 534 may be a fan beam, subtending typically 30°. The spectrum of beam 534 is shaped in accordance with the teachings above referring to FIGS. 5 and 6A–6C. The transmission x-ray source from a linear accelerator is inherently pulsed, with typical pulse rates in the range between 100 and 400 pulses per second. The portion of transmission beam 534 which traverses enclosure 32 and objects 530 and 538 contained within the enclosure is detected by transmission detector 540 which may be coupled to the inspection modules 508 and 510 by means of gantry 550 (shown in FIG. 13). Sources 536, 515, and 520 produce respective beams that are spatially staggered so that a given object within the enclosure passes successively through the beams as the inspection module 504 passes along tracks 506 with respect to stationary enclosure 32. In accordance with other embodiments of the present invention, the backscatter signals and transmission signals may also be rendered completely independent of one another by temporal gating of the different detectors.

The electrical output signals produced by detectors 526, 528, and 540 are processed by processor 542 to derive characteristics such as the geometry, position, density, mass, and effective atomic number of the contents from the scatter signals and transmission signals using algorithms known to persons skilled in the art of x-ray inspection. In particular, images of the contents of enclosure 32 may be produced by an image generator. As used in this description and in the appended claims, the term "image" refers to an ordered representation of detector signals corresponding to spatial positions. For example, the image may be an array of values within an electronic memory, or, alternatively, a visual image may be formed on a display device 544 such as a video screen or printer. The use of algorithms, as known in the art of x-ray inspection, for identifying suspect regions within the enclosure, and identification of the presence of a specified condition by means of an alarm or otherwise, is within the scope of the present invention.

In many applications, it is desirable that enclosure 32 be inspected in a single pass of the inspection module 504 past the enclosure 32 in direction 501.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A graduated collimating aperture for providing a beam of increasing average energy as a function of distance measured from a central axis, the collimating aperture comprising a plurality of concentric areas, each of the areas defined in a plane substantially perpendicular to the central axis, such that any specified area is characterized by an opacity to the beam exceeding that of any area interior to the specified area.

2. The graduated collimating aperture according to claim 1, wherein at least one of the plurality of concentric areas is the surface of an x-ray attenuating material.

3. The graduated collimating aperture according to claim 1, wherein the plurality of concentric areas includes a central area of substantially no attenuation.

4. The graduated collimating aperture according to claim 1, wherein a subset of the plurality of concentric areas comprise, surfaces of frames of radially increasing opacity.

5. An inspection system for inspecting an object, the system comprising:
   a. a source for generating a penetrating radiation beam for irradiating the object, the beam having, at each instant of time, an instantaneous power spectrum of intensity as a function of energy;
   b. a shaper for modulating the generated beam, thereby creating a shaped beam, the shaper comprising at least a first section and a second section, the first section attenuating the intensity of a portion of the generated beam by a first attenuation factor and the second section attenuating the intensity of another portion of the generated beam by a second attenuation factor;
   c. a scanner for scanning the first and second sections of the penetrating radiation beam with respect to the inspected object and
   d. at least one detector for detecting the shaped beam after the shaped beam interacts with the object wherein the shaper spatially separates the shaped beam into a first beam and a second beam, the first beam including the portion of the generated beam attenuated in the first section of the shaper and the second beam including the portion of the generated beam attenuated in the second section of the shaper.

6. The inspection system according to claim 5, wherein the at least one detector detects the first beam after the first beam interacts with the object, further comprising a second detector for detecting the second beam after the second beam interacts with the object.

7. The inspection system according to claim 6, wherein the at least one detector further detects photons of energies in the first beam exceeding a first fiducial energy and wherein the second detector further detects photons of energies in the second beam exceeding a second fiducial energy.

* * * * *